(12) United States Patent (10) Patent No.: US 8,808,369 B2
Suri (45) Date of Patent: Aug. 19, 2014

(54) MINIMALLY INVASIVE AORTIC VALVE REPLACEMENT

(75) Inventor: Rakesh M. Suri, Rochester, MN (US)

(73) Assignee: Mayo Foundation for Medical Education and Research, Rochester, NY (US)

( * ) Notice: Subject to any disclaimer, the term of this patent is extended or adjusted under 35 U.S.C. 154(b) by 227 days.

(21) Appl. No.: 12/897,937

(22) Filed: Oct. 5, 2010

(65) Prior Publication Data

US 2011/0082539 A1 Apr. 7, 2011

Related U.S. Application Data

(60) Provisional application No. 61/248,742, filed on Oct. 5, 2009.

(51) Int. Cl.
*A61F 2/24* (2006.01)
*A61B 17/34* (2006.01)

(52) U.S. Cl.
CPC ............ *A61F 2/2418* (2013.01); *A61F 2/2436* (2013.01); *A61F 2/243* (2013.01); *A61B 2017/3466* (2013.01)
USPC .......... 623/2.11; 623/2.1; 623/2.38; 623/2.39

(58) Field of Classification Search
USPC ............. 623/2.11, 2.1, 21.7, 2.14, 1.11, 1.23, 623/1.24, 904, 2.38, 2.39, 2.4; 128/898
See application file for complete search history.

(56) References Cited

U.S. PATENT DOCUMENTS

| 3,143,742 A | 8/1964 | Cromie |
| 3,334,629 A | 8/1967 | Cohn |
| 3,409,013 A | 11/1968 | Berry |
| 3,540,431 A | 11/1970 | Mobin-Uddin |
| 3,546,710 A | 12/1970 | Shumakov et al. |
| 3,574,865 A | 4/1971 | Hamaker |
| 3,587,115 A | 6/1971 | Shiley |
| 3,608,097 A | 9/1971 | Bellhouse et al. |
| 3,628,535 A | 12/1971 | Ostrowsky et al. |

(Continued)

FOREIGN PATENT DOCUMENTS

| CN | 2007/10007443 | 8/2007 |
| DE | 3640745 | 6/1987 |

(Continued)

OTHER PUBLICATIONS

European Search Report issued in EP Application No. 05004289, dated Jun. 2, 2005, 3 pages.

(Continued)

*Primary Examiner* — Corrine M McDermott
*Assistant Examiner* — Jing Ou
(74) *Attorney, Agent, or Firm* — Faegre Baker Daniels LLP

(57) ABSTRACT

A minimally invasive method of implanting a prosthetic aortic valve includes forming a surgical site within a patient's chest that includes a first access port, a second access port, a viewing port and a delivery port. A camera is inserted into the viewing port. The native aortic valve leaflets may each be grasped and removed via tools inserted through the first and second access ports. The prosthetic aortic valve may be delivered through the delivery port to the valve annulus using a delivery device. The prosthetic aortic valve is implanted at the valve annulus and the delivery device is withdrawn. A surgeon may perform the remotely operated steps while viewing images provided by the camera.

13 Claims, 15 Drawing Sheets

(56) References Cited

U.S. PATENT DOCUMENTS

| | | | |
|---|---|---|---|
| 3,642,004 | A | 2/1972 | Osthagen et al. |
| 3,657,744 | A | 4/1972 | Ersek |
| 3,671,979 | A | 6/1972 | Moulopoulos |
| 3,744,060 | A | 7/1973 | Bellhouse et al. |
| 3,755,823 | A | 9/1973 | Hancock |
| 3,795,246 | A | 3/1974 | Sturgeon |
| 3,839,741 | A | 10/1974 | Haller |
| 3,868,956 | A | 3/1975 | Alfidi et al. |
| 3,874,388 | A | 4/1975 | King et al. |
| 3,997,923 | A | 12/1976 | Possis |
| 4,035,849 | A | 7/1977 | Angell et al. |
| 4,056,854 | A | 11/1977 | Boretos et al. |
| 4,086,665 | A | 5/1978 | Poirier |
| 4,106,129 | A | 8/1978 | Carpentier et al. |
| 4,222,126 | A | 9/1980 | Boretos et al. |
| 4,233,690 | A | 11/1980 | Akins |
| 4,265,694 | A | 5/1981 | Boretos |
| 4,291,420 | A | 9/1981 | Reul |
| 4,297,749 | A | 11/1981 | Davis et al. |
| 4,339,831 | A | 7/1982 | Johnson |
| 4,343,048 | A | 8/1982 | Ross et al. |
| 4,345,340 | A | 8/1982 | Rosen |
| 4,425,908 | A | 1/1984 | Simon |
| 4,451,936 | A | 6/1984 | Carpentier et al. |
| 4,470,157 | A | 9/1984 | Love |
| 4,477,930 | A | 10/1984 | Totten et al. |
| 4,501,030 | A | 2/1985 | Lane |
| 4,506,394 | A | 3/1985 | Bedard |
| 4,574,803 | A | 3/1986 | Storz |
| 4,580,568 | A | 4/1986 | Gianturco |
| 4,592,340 | A | 6/1986 | Boyles |
| 4,610,688 | A | 9/1986 | Silvestrini et al. |
| 4,612,011 | A | 9/1986 | Kautzky |
| 4,624,822 | A | 11/1986 | Arru et al. |
| 4,647,283 | A | 3/1987 | Carpentier et al. |
| 4,648,881 | A | 3/1987 | Carpentier et al. |
| 4,655,218 | A | 4/1987 | Kulik et al. |
| 4,655,771 | A | 4/1987 | Wallsten |
| 4,662,885 | A | 5/1987 | DiPisa, Jr. |
| 4,665,906 | A | 5/1987 | Jervis |
| 4,681,908 | A | 7/1987 | Broderick et al. |
| 4,692,164 | A | 9/1987 | Dzemeshkevich et al. |
| 4,710,192 | A | 12/1987 | Liotta et al. |
| 4,733,665 | A | 3/1988 | Palmaz |
| 4,758,151 | A | 7/1988 | Arru et al. |
| 4,777,951 | A | 10/1988 | Cribier et al. |
| 4,787,899 | A | 11/1988 | Lazarus |
| 4,796,629 | A | 1/1989 | Grayzel |
| 4,797,901 | A | 1/1989 | Goerne et al. |
| 4,819,751 | A | 4/1989 | Shimada et al. |
| 4,834,755 | A | 5/1989 | Silvestrini et al. |
| 4,856,516 | A | 8/1989 | Hillstead |
| 4,872,874 | A | 10/1989 | Taheri |
| 4,878,495 | A | 11/1989 | Grayzel |
| 4,878,906 | A | 11/1989 | Lindemann et al. |
| 4,883,458 | A | 11/1989 | Shiber |
| 4,909,252 | A | 3/1990 | Goldberger |
| 4,917,102 | A | 4/1990 | Miller et al. |
| 4,922,905 | A | 5/1990 | Strecker |
| 4,954,126 | A | 9/1990 | Wallsten |
| 4,966,604 | A | 10/1990 | Reiss |
| 4,979,939 | A | 12/1990 | Shiber |
| 4,986,830 | A | 1/1991 | Owens et al. |
| 4,994,077 | A | 2/1991 | Dobben |
| 5,002,559 | A | 3/1991 | Tower |
| 5,007,896 | A | 4/1991 | Shiber |
| 5,026,366 | A | 6/1991 | Leckrone |
| 5,032,128 | A | 7/1991 | Alonso |
| 5,037,434 | A | 8/1991 | Lane |
| 5,047,041 | A | 9/1991 | Samuels |
| 5,059,177 | A | 10/1991 | Towne et al. |
| 5,061,273 | A | 10/1991 | Yock |
| 5,084,151 | A | 1/1992 | Vallana et al. |
| 5,085,635 | A | 2/1992 | Cragg |
| 5,089,015 | A | 2/1992 | Ross |
| 5,123,919 | A | 6/1992 | Sauter et al. |
| 5,133,845 | A | 7/1992 | Vallana et al. |
| 5,139,515 | A | 8/1992 | Robicsek |
| 5,152,771 | A | 10/1992 | Sabbaghian et al. |
| 5,161,547 | A | 11/1992 | Tower |
| 5,163,953 | A | 11/1992 | Vince |
| 5,163,954 | A | 11/1992 | Curcio et al. |
| 5,167,628 | A | 12/1992 | Boyles |
| 5,217,483 | A | 6/1993 | Tower |
| 5,232,445 | A | 8/1993 | Bonzel |
| 5,272,909 | A | 12/1993 | Nguyen et al. |
| 5,295,958 | A | 3/1994 | Shturman |
| 5,300,086 | A | 4/1994 | Gory et al. |
| 5,314,468 | A | 5/1994 | Martinez et al. |
| 5,327,774 | A | 7/1994 | Nguyen et al. |
| 5,332,402 | A | 7/1994 | Teitelbaum |
| 5,350,398 | A | 9/1994 | Pavcnik et al. |
| 5,370,684 | A | 12/1994 | Vallana et al. |
| 5,370,685 | A | 12/1994 | Stevens |
| 5,387,247 | A | 2/1995 | Vallana et al. |
| 5,389,106 | A | 2/1995 | Tower |
| 5,397,351 | A | 3/1995 | Pavcnik et al. |
| 5,411,552 | A | 5/1995 | Andersen et al. |
| 5,415,633 | A | 5/1995 | Lazarus et al. |
| 5,423,886 | A | 6/1995 | Arru et al. |
| 5,431,676 | A | 7/1995 | Dubrul et al. |
| 5,443,446 | A | 8/1995 | Shturman |
| 5,449,384 | A | 9/1995 | Johnson |
| 5,480,424 | A | 1/1996 | Cox |
| 5,489,294 | A | 2/1996 | McVenes et al. |
| 5,489,297 | A | 2/1996 | Duran |
| 5,496,346 | A | 3/1996 | Horzewski et al. |
| 5,507,767 | A | 4/1996 | Maeda et al. |
| 5,545,209 | A | 8/1996 | Roberts et al. |
| 5,545,211 | A | 8/1996 | An et al. |
| 5,545,214 | A | 8/1996 | Stevens |
| 5,545,215 | A | 8/1996 | Duran |
| 5,554,185 | A | 9/1996 | Block et al. |
| 5,575,818 | A | 11/1996 | Pinchuk |
| 5,580,922 | A | 12/1996 | Park et al. |
| 5,591,195 | A | 1/1997 | Taheri et al. |
| 5,609,626 | A | 3/1997 | Quijano et al. |
| 5,645,559 | A | 7/1997 | Hachtman et al. |
| 5,665,115 | A | 9/1997 | Cragg |
| 5,667,523 | A | 9/1997 | Bynon et al. |
| 5,674,277 | A | 10/1997 | Freitag |
| 5,695,498 | A | 12/1997 | Tower |
| 5,702,368 | A | 12/1997 | Stevens et al. |
| 5,712,953 | A | 1/1998 | Langs |
| 5,713,953 | A | 2/1998 | Vallana et al. |
| 5,716,417 | A | 2/1998 | Girard et al. |
| 5,746,709 | A | 5/1998 | Rom et al. |
| 5,749,890 | A | 5/1998 | Shaknovich |
| 5,766,151 | A | 6/1998 | Valley et al. |
| 5,782,809 | A | 7/1998 | Umeno et al. |
| 5,800,456 | A | 9/1998 | Maeda et al. |
| 5,800,508 | A | 9/1998 | Goicoechea et al. |
| 5,807,405 | A | 9/1998 | Vanney et al. |
| 5,817,126 | A | 10/1998 | Imran |
| 5,824,037 | A | 10/1998 | Fogarty et al. |
| 5,824,041 | A | 10/1998 | Lenker |
| 5,824,043 | A | 10/1998 | Cottone, Jr. |
| 5,824,053 | A | 10/1998 | Khosravi et al. |
| 5,824,056 | A | 10/1998 | Rosenberg |
| 5,824,061 | A | 10/1998 | Quijano et al. |
| 5,824,064 | A | 10/1998 | Taheri |
| 5,840,081 | A | 11/1998 | Andersen et al. |
| 5,843,158 | A | 12/1998 | Lenker et al. |
| 5,843,244 | A | 12/1998 | Pelton et al. |
| 5,851,232 | A | 12/1998 | Lois |
| 5,855,597 | A | 1/1999 | Jayaraman |
| 5,855,601 | A | 1/1999 | Bessler et al. |
| 5,860,966 | A | 1/1999 | Tower |
| 5,861,028 | A | 1/1999 | Angell |
| 5,868,783 | A | 2/1999 | Tower |
| 5,876,436 | A | 3/1999 | Vanney et al. |
| 5,876,448 | A | 3/1999 | Thompson et al. |
| 5,888,201 | A | 3/1999 | Stinson et al. |
| 5,891,191 | A | 4/1999 | Stinson |

(56) References Cited

U.S. PATENT DOCUMENTS

| | | |
|---|---|---|
| 5,891,195 A | 4/1999 | Klostermeyer et al. |
| 5,906,619 A | 5/1999 | Olson et al. |
| 5,907,893 A | 6/1999 | Zadno-Azizi et al. |
| 5,913,842 A | 6/1999 | Boyd et al. |
| 5,925,063 A | 7/1999 | Khosravi |
| 5,944,738 A | 8/1999 | Amplatz et al. |
| 5,954,766 A | 9/1999 | Zadno Azizi et al. |
| 5,957,949 A | 9/1999 | Leonhardt et al. |
| 5,968,068 A | 10/1999 | Dehdashtian et al. |
| 5,980,570 A | 11/1999 | Simpson |
| 5,984,957 A | 11/1999 | Laptewicz, Jr. et al. |
| 5,997,573 A | 12/1999 | Quijano et al. |
| 6,010,531 A * | 1/2000 | Donlon et al. ............. 623/2.1 |
| 6,019,790 A | 2/2000 | Holmberg et al. |
| 6,022,370 A | 2/2000 | Tower |
| 6,027,525 A | 2/2000 | Suh et al. |
| 6,029,671 A | 2/2000 | Stevens et al. |
| 6,042,589 A | 3/2000 | Marianne |
| 6,042,598 A | 3/2000 | Tsugita et al. |
| 6,042,607 A | 3/2000 | Williamson, IV |
| 6,051,014 A | 4/2000 | Jang |
| 6,059,809 A | 5/2000 | Amor et al. |
| 6,059,827 A | 5/2000 | Fenton, Jr. |
| 6,110,201 A | 8/2000 | Quijano et al. |
| 6,146,366 A | 11/2000 | Schachar |
| 6,159,239 A | 12/2000 | Greenhalgh |
| 6,162,208 A | 12/2000 | Hipps |
| 6,162,245 A | 12/2000 | Jayaraman |
| 6,168,614 B1 | 1/2001 | Andersen et al. |
| 6,171,335 B1 | 1/2001 | Wheatley et al. |
| 6,187,016 B1 | 2/2001 | Hedges et al. |
| 6,197,143 B1 | 3/2001 | Bodnar |
| 6,200,336 B1 | 3/2001 | Pavcnik et al. |
| 6,203,550 B1 | 3/2001 | Olson |
| 6,210,408 B1 | 4/2001 | Chandrasekaran et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 | 6/2001 | Jayaraman |
| 6,248,116 B1 | 6/2001 | Chevilon |
| 6,258,114 B1 | 7/2001 | Konya et al. |
| 6,258,115 B1 | 7/2001 | Dubrul |
| 6,258,120 B1 | 7/2001 | McKenzie et al. |
| 6,270,526 B1 | 8/2001 | Cox |
| 6,277,555 B1 | 8/2001 | Duran et al. |
| 6,287,339 B1 * | 9/2001 | Vazquez et al. ............. 623/2.4 |
| 6,299,637 B1 | 10/2001 | Shaolia et al. |
| 6,299,638 B1 | 10/2001 | Sauter |
| 6,302,906 B1 | 10/2001 | Goicoechea et al. |
| 6,309,382 B1 | 10/2001 | Garrison et al. |
| 6,309,417 B1 | 10/2001 | Spence et al. |
| 6,312,462 B1 | 11/2001 | McDermott et al. |
| 6,338,735 B1 | 1/2002 | Stevens |
| 6,348,063 B1 | 2/2002 | Yassour et al. |
| 6,350,277 B1 | 2/2002 | Kocur |
| 6,352,554 B2 | 3/2002 | De Paulis |
| 6,352,708 B1 | 3/2002 | Duran et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,398,807 B1 | 6/2002 | Chouinard et al. |
| 6,402,780 B2 | 6/2002 | Williamson et al. |
| 6,409,750 B1 | 6/2002 | Hyodoh et al. |
| 6,424,885 B1 | 7/2002 | Niemeyer et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,475,239 B1 | 11/2002 | Campbell et al. |
| 6,482,228 B1 | 11/2002 | Norred |
| 6,488,704 B1 | 12/2002 | Connelly et al. |
| 6,493,608 B1 | 12/2002 | Niemeyer |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. |
| 6,530,949 B2 | 3/2003 | Konya et al. |
| 6,544,285 B1 | 4/2003 | Thubrikar et al. |
| 6,562,031 B2 | 5/2003 | Chandrasekaran et al. |
| 6,562,058 B2 | 5/2003 | Seguin et al. |
| 6,569,196 B1 | 5/2003 | Vesely |
| 6,582,462 B1 | 6/2003 | Andersen et al. |
| 6,585,758 B1 | 7/2003 | Chouinard et al. |
| 6,592,546 B1 | 7/2003 | Barbut et al. |
| 6,605,112 B1 | 8/2003 | Moll et al. |
| 6,613,077 B2 | 9/2003 | Gilligan et al. |
| 6,622,604 B1 | 9/2003 | Chouinard et al. |
| 6,635,068 B1 | 10/2003 | Dubrul et al. |
| 6,652,571 B1 | 11/2003 | White et al. |
| 6,652,578 B2 | 11/2003 | Bailey et al. |
| 6,656,213 B2 | 12/2003 | Solem |
| 6,656,219 B1 | 12/2003 | Wiktor |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,684 B1 | 1/2004 | Morley et al. |
| 6,676,692 B2 | 1/2004 | Rabkin et al. |
| 6,676,698 B2 | 1/2004 | McGuckin, Jr. et al. |
| 6,679,893 B1 | 1/2004 | Tran |
| 6,682,558 B2 | 1/2004 | Tu et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,769,434 B2 | 8/2004 | Liddicoat et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,792,979 B2 | 9/2004 | Konya et al. |
| 6,797,002 B2 | 9/2004 | Spence |
| 6,805,711 B2 | 10/2004 | Quijano et al. |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof et al. |
| 6,846,325 B2 | 1/2005 | Liddicoat |
| 6,866,650 B2 | 3/2005 | Stevens |
| 6,872,223 B2 | 3/2005 | Roberts |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,929,653 B2 | 8/2005 | Strecter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,974,474 B2 | 12/2005 | Pavcnik et al. |
| 6,974,476 B2 | 12/2005 | McGuckin et al. |
| 6,986,742 B2 | 1/2006 | Hart et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,018,401 B1 | 3/2006 | Hyodoh et al. |
| 7,018,404 B2 | 3/2006 | Holmberg et al. |
| 7,018,406 B2 | 3/2006 | Seguin et al. |

(56) References Cited

U.S. PATENT DOCUMENTS

| | | |
|---|---|---|
| 7,041,128 B2 | 5/2006 | McGuckin, Jr. et al. |
| 7,044,966 B2 | 5/2006 | Svanidze et al. |
| 7,048,014 B2 | 5/2006 | Hyodoh et al. |
| 7,097,659 B2 | 8/2006 | Woolfson et al. |
| 7,105,016 B2 | 9/2006 | Shiu et al. |
| 7,115,141 B2 | 10/2006 | Menz et al. |
| 7,125,418 B2 | 10/2006 | Duran et al. |
| 7,128,759 B2 | 10/2006 | Osborne et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,211,107 B2 | 5/2007 | Bruckheimer et al. |
| 7,252,682 B2 | 8/2007 | Seguin |
| 7,255,706 B2 | 8/2007 | Rosengart |
| 7,261,732 B2 | 8/2007 | Justino |
| 7,276,078 B2 | 10/2007 | Spenser et al. |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin et al. |
| 7,329,279 B2 | 2/2008 | Haug et al. |
| 7,335,218 B2 | 2/2008 | Wilson et al. |
| 7,338,520 B2 | 3/2008 | Bailey et al. |
| 7,347,869 B2 | 3/2008 | Hojeibane et al. |
| 7,351,256 B2 | 4/2008 | Hojeibane et al. |
| 7,374,571 B2 | 5/2008 | Pease et al. |
| 7,377,938 B2 | 5/2008 | Sarac et al. |
| 7,377,941 B2 | 5/2008 | Rhee et al. |
| 7,381,218 B2 | 6/2008 | Schreck |
| 7,384,411 B1 | 6/2008 | Condado |
| 7,393,360 B2 | 7/2008 | Spenser et al. |
| 7,429,269 B2 | 9/2008 | Schwammenthal et al. |
| 7,442,204 B2 | 10/2008 | Schwammenthal et al. |
| 7,453,227 B2 | 11/2008 | Prisco et al. |
| 7,462,191 B2 | 12/2008 | Spenser et al. |
| 7,470,284 B2 | 12/2008 | Lambrecht et al. |
| 7,481,838 B2 | 1/2009 | Carpentier et al. |
| 7,534,259 B2 | 5/2009 | Lashinski et al. |
| 7,544,206 B2 | 6/2009 | Cohn et al. |
| 7,547,322 B2 | 6/2009 | Sarac et al. |
| 7,556,645 B2 | 7/2009 | Lashinski et al. |
| 7,556,646 B2 | 7/2009 | Yang et al. |
| 7,569,071 B2 | 8/2009 | Haverkost et al. |
| 7,578,843 B2 | 8/2009 | Shu |
| 7,585,321 B2 | 9/2009 | Cribier |
| 7,591,848 B2 | 9/2009 | Allen |
| 7,618,446 B2 | 11/2009 | Andersen et al. |
| 7,618,447 B2 | 11/2009 | Case et al. |
| 7,682,390 B2 | 3/2010 | Seguin |
| 7,708,775 B2 | 5/2010 | Rowe et al. |
| 7,780,726 B2 | 8/2010 | Seguin |
| 7,806,919 B2 | 10/2010 | Bloom et al. |
| 7,981,153 B2 * | 7/2011 | Fogarty et al. .............. 623/2.38 |
| 8,083,793 B2 * | 12/2011 | Lane et al. .................. 623/2.38 |
| 8,109,996 B2 | 2/2012 | Stacchino et al. |
| 2001/0001314 A1 | 5/2001 | Davison et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0011189 A1 | 8/2001 | Drasler et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044647 A1 | 11/2001 | Pinchuk et al. |
| 2002/0010508 A1 | 1/2002 | Chobotov |
| 2002/0029014 A1 | 3/2002 | Jayaraman |
| 2002/0029783 A1 * | 3/2002 | Stevens et al. ............... 128/898 |
| 2002/0032480 A1 | 3/2002 | Spence et al. |
| 2002/0032481 A1 | 3/2002 | Gabbay |
| 2002/0035396 A1 | 3/2002 | Heath |
| 2002/0042650 A1 | 4/2002 | Vardi et al. |
| 2002/0042651 A1 | 4/2002 | Liddicoat et al. |
| 2002/0058994 A1 | 5/2002 | Hill et al. |
| 2002/0058995 A1 | 5/2002 | Stevens |
| 2002/0072789 A1 | 6/2002 | Hackett et al. |
| 2002/0095209 A1 | 7/2002 | Zadno-Azizi et al. |
| 2002/0103533 A1 | 8/2002 | Langberg et al. |
| 2002/0107565 A1 | 8/2002 | Greenhalgh |
| 2002/0111674 A1 | 8/2002 | Chouinard et al. |
| 2002/0123802 A1 | 9/2002 | Snyders |
| 2002/0128702 A1 | 9/2002 | Menz et al. |
| 2002/0133183 A1 | 9/2002 | Lentz et al. |
| 2002/0133226 A1 | 9/2002 | Marquez et al. |
| 2002/0138138 A1 | 9/2002 | Yang |
| 2002/0151970 A1 | 10/2002 | Garrison et al. |
| 2002/0161377 A1 | 10/2002 | Rabkin |
| 2002/0161392 A1 | 10/2002 | Dubrul |
| 2002/0161394 A1 | 10/2002 | Macoviak et al. |
| 2002/0183839 A1 * | 12/2002 | Garrison et al. .............. 623/2.11 |
| 2002/0193871 A1 | 12/2002 | Beyersdorf et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0028247 A1 | 2/2003 | Cali |
| 2003/0036791 A1 | 2/2003 | Bonhoeffer et al. |
| 2003/0036795 A1 | 2/2003 | Andersen et al. |
| 2003/0040771 A1 | 2/2003 | Hyodoh et al. |
| 2003/0040772 A1 | 2/2003 | Hyodoh et al. |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0109924 A1 | 6/2003 | Cribier |
| 2003/0125795 A1 | 7/2003 | Pavcnik et al. |
| 2003/0130726 A1 | 7/2003 | Thorpe et al. |
| 2003/0130729 A1 | 7/2003 | Paniagua et al. |
| 2003/0139804 A1 | 7/2003 | Hankh et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0163194 A1 | 8/2003 | Quijano et al. |
| 2003/0181850 A1 | 9/2003 | Diamond et al. |
| 2003/0191519 A1 | 10/2003 | Lombardi et al. |
| 2003/0191528 A1 | 10/2003 | Quijano et al. |
| 2003/0199913 A1 | 10/2003 | Dubrul et al. |
| 2003/0199963 A1 | 10/2003 | Tower et al. |
| 2003/0208261 A1 | 11/2003 | Thorpe et al. |
| 2003/0212410 A1 | 11/2003 | Stenzel et al. |
| 2003/0212454 A1 | 11/2003 | Scott et al. |
| 2003/0225445 A1 | 12/2003 | Derus et al. |
| 2004/0019374 A1 | 1/2004 | Hojeibane et al. |
| 2004/0034407 A1 | 2/2004 | Sherry |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0055606 A1 | 3/2004 | Hendricksen et al. |
| 2004/0073301 A1 * | 4/2004 | Donlon et al. ............... 623/2.11 |
| 2004/0078072 A1 | 4/2004 | Tu et al. |
| 2004/0078074 A1 | 4/2004 | Anderson et al. |
| 2004/0082904 A1 | 4/2004 | Houde et al. |
| 2004/0088045 A1 | 5/2004 | Cox |
| 2004/0092858 A1 | 5/2004 | Wilson et al. |
| 2004/0092989 A1 | 5/2004 | Wilson et al. |
| 2004/0093005 A1 | 5/2004 | Durcan |
| 2004/0093060 A1 | 5/2004 | Seguin et al. |
| 2004/0093070 A1 | 5/2004 | Hojeibane et al. |
| 2004/0093075 A1 | 5/2004 | Kuehne |
| 2004/0097788 A1 | 5/2004 | Mourles et al. |
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |

(56) References Cited

U.S. PATENT DOCUMENTS

| | | |
|---|---|---|
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122514 A1 | 6/2004 | Fogarty et al. |
| 2004/0122516 A1 | 6/2004 | Fogarty |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson |
| 2004/0167620 A1 | 8/2004 | Ortiz |
| 2004/0186558 A1 | 9/2004 | Pavenik et al. |
| 2004/0186563 A1 | 9/2004 | Iobbi |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210307 A1 | 10/2004 | Khairkhahan |
| 2004/0215333 A1 | 10/2004 | Duran |
| 2004/0215339 A1 | 10/2004 | Drasler et al. |
| 2004/0225353 A1 | 11/2004 | McGuckin, Jr. |
| 2004/0225354 A1 | 11/2004 | Allen |
| 2004/0225355 A1 | 11/2004 | Stevens |
| 2004/0254636 A1 | 12/2004 | Flagle et al. |
| 2004/0260389 A1 | 12/2004 | Case et al. |
| 2004/0260394 A1 | 12/2004 | Douk et al. |
| 2004/0267357 A1 | 12/2004 | Allen et al. |
| 2005/0010246 A1 | 1/2005 | Streeter |
| 2005/0010285 A1 | 1/2005 | Lambrecht et al. |
| 2005/0010287 A1 | 1/2005 | Macoviak |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto |
| 2005/0049696 A1 | 3/2005 | Siess |
| 2005/0055088 A1 | 3/2005 | Liddicoat et al. |
| 2005/0060029 A1 | 3/2005 | Le |
| 2005/0060030 A1 | 3/2005 | Lashinski et al. |
| 2005/0075584 A1 | 4/2005 | Cali |
| 2005/0075712 A1 | 4/2005 | Biancucci et al. |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0075726 A1 | 4/2005 | Svanidze et al. |
| 2005/0075727 A1 | 4/2005 | Wheatley |
| 2005/0075728 A1 | 4/2005 | Nguyen et al. |
| 2005/0075729 A1 | 4/2005 | Nguyen et al. |
| 2005/0075730 A1 | 4/2005 | Myers et al. |
| 2005/0075731 A1 | 4/2005 | Artof et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0107871 A1 | 5/2005 | Realyvasquez et al. |
| 2005/0113910 A1 | 5/2005 | Paniagua |
| 2005/0119688 A1 | 6/2005 | Bergheim |
| 2005/0131438 A1 | 6/2005 | Cohn |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0143807 A1 | 6/2005 | Pavcnik et al. |
| 2005/0143809 A1 | 6/2005 | Salahieh et al. |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0187616 A1 | 8/2005 | Realyvasquez |
| 2005/0197695 A1 | 9/2005 | Stacchino et al. |
| 2005/0203549 A1 | 9/2005 | Realyvasquez |
| 2005/0203605 A1 | 9/2005 | Dolan |
| 2005/0203618 A1 | 9/2005 | Sharkawy |
| 2005/0222674 A1 | 10/2005 | Paine |
| 2005/0222675 A1 | 10/2005 | Sauter |
| 2005/0228495 A1 | 10/2005 | Macoviak |
| 2005/0234546 A1 | 10/2005 | Nugent et al. |
| 2005/0240200 A1 | 10/2005 | Bergheim |
| 2005/0240263 A1 | 10/2005 | Fogarty et al. |
| 2005/0261759 A1 | 11/2005 | Lambrecht et al. |
| 2005/0283962 A1 | 12/2005 | Boudjemline |
| 2006/0004439 A1 | 1/2006 | Spenser et al. |
| 2006/0004442 A1 | 1/2006 | Spenser et al. |
| 2006/0004469 A1 | 1/2006 | Sokel |
| 2006/0009841 A1 | 1/2006 | McGuckin et al. |
| 2006/0025855 A1 | 2/2006 | Lashinski et al. |
| 2006/0052867 A1 | 3/2006 | Revuelta et al. |
| 2006/0058775 A1 | 3/2006 | Stevens et al. |
| 2006/0058872 A1 | 3/2006 | Salahieh et al. |
| 2006/0085060 A1 | 4/2006 | Campbell |
| 2006/0089711 A1 | 4/2006 | Dolan |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0167474 A1 | 7/2006 | Bloom et al. |
| 2006/0178740 A1 | 8/2006 | Stacchino et al. |
| 2006/0190017 A1 | 8/2006 | Cyr et al. |
| 2006/0195134 A1 | 8/2006 | Crittenden |
| 2006/0195184 A1 | 8/2006 | Lane et al. |
| 2006/0206192 A1 | 9/2006 | Tower et al. |
| 2006/0206202 A1 | 9/2006 | Bonhoefer et al. |
| 2006/0212111 A1 | 9/2006 | Case et al. |
| 2006/0247763 A1 | 11/2006 | Slater |
| 2006/0253134 A1 | 11/2006 | Ortiz et al. |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0271166 A1 | 11/2006 | Thill et al. |
| 2006/0271175 A1 | 11/2006 | Woolfson et al. |
| 2006/0276874 A1 | 12/2006 | Wilson et al. |
| 2006/0276882 A1 | 12/2006 | Case et al. |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010878 A1 | 1/2007 | Rafiee et al. |
| 2007/0016286 A1 | 1/2007 | Herrmann et al. |
| 2007/0027518 A1 | 2/2007 | Case et al. |
| 2007/0027533 A1 | 2/2007 | Douk |
| 2007/0032850 A1 | 2/2007 | Ruiz et al. |
| 2007/0038295 A1 | 2/2007 | Case et al. |
| 2007/0043431 A1 | 2/2007 | Melsheimer |
| 2007/0043435 A1 | 2/2007 | Seguin et al. |
| 2007/0051377 A1 | 3/2007 | Douk et al. |
| 2007/0073387 A1 | 3/2007 | Forster et al. |
| 2007/0073392 A1 | 3/2007 | Heynick-Janitz |
| 2007/0078509 A1 | 4/2007 | Lotfy et al. |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0093887 A1 | 4/2007 | Case et al. |
| 2007/0093890 A1 | 4/2007 | Eliasen et al. |
| 2007/0100432 A1 | 5/2007 | Case et al. |

(56) References Cited

U.S. PATENT DOCUMENTS

| | | |
|---|---|---|
| 2007/0100435 A1 | 5/2007 | Case et al. |
| 2007/0100439 A1 | 5/2007 | Cangialosi |
| 2007/0100440 A1 | 5/2007 | Figulla et al. |
| 2007/0100449 A1 | 5/2007 | O'Neil et al. |
| 2007/0106372 A1 | 5/2007 | Osborne et al. |
| 2007/0112415 A1 | 5/2007 | Bartlett |
| 2007/0112422 A1 | 5/2007 | Dehdashtian |
| 2007/0118209 A1 | 5/2007 | Strecker |
| 2007/0118215 A1 | 5/2007 | Moaddeb |
| 2007/0142968 A1* | 6/2007 | Prisco et al. ............... 700/245 |
| 2007/0162102 A1 | 7/2007 | Ryan et al. |
| 2007/0162113 A1 | 7/2007 | Sharkawy et al. |
| 2007/0168024 A1 | 7/2007 | Khairkhahan |
| 2007/0185513 A1 | 8/2007 | Woolfson et al. |
| 2007/0203391 A1 | 8/2007 | Bloom et al. |
| 2007/0203503 A1 | 8/2007 | Salahieh et al. |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0237802 A1 | 10/2007 | McKay et al. |
| 2007/0238979 A1 | 10/2007 | Huynh et al. |
| 2007/0239254 A1 | 10/2007 | Marchand et al. |
| 2007/0239265 A1 | 10/2007 | Birdsall et al. |
| 2007/0239266 A1 | 10/2007 | Birdsall |
| 2007/0239269 A1 | 10/2007 | Dolan et al. |
| 2007/0239271 A1 | 10/2007 | Nguyen |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0288000 A1 | 12/2007 | Bonan |
| 2007/0293942 A1 | 12/2007 | Mirzaee |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0048656 A1 | 2/2008 | Tan |
| 2008/0065011 A1 | 3/2008 | Marchand et al. |
| 2008/0065204 A1 | 3/2008 | Macoviak et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0077234 A1 | 3/2008 | Styrc |
| 2008/0082164 A1 | 4/2008 | Friedman |
| 2008/0082165 A1 | 4/2008 | Wilson et al. |
| 2008/0082166 A1 | 4/2008 | Styrc et al. |
| 2008/0097595 A1 | 4/2008 | Gabbay |
| 2008/0103586 A1 | 5/2008 | Styrc et al. |
| 2008/0125859 A1 | 5/2008 | Salahieh et al. |
| 2008/0133033 A1 | 6/2008 | Wolff et al. |
| 2008/0140189 A1 | 6/2008 | Nguyen et al. |
| 2008/0147105 A1 | 6/2008 | Wilson et al. |
| 2008/0147160 A1 | 6/2008 | Ghione et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1 | 6/2008 | Benichow et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0188880 A1 | 8/2008 | Fischer et al. |
| 2008/0188928 A1 | 8/2008 | Salahieh et al. |
| 2008/0215143 A1 | 9/2008 | Seguin et al. |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0249619 A1 | 10/2008 | Stacchino et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0255662 A1 | 10/2008 | Stacchino et al. |
| 2008/0262593 A1 | 10/2008 | Ryan et al. |
| 2008/0269878 A1 | 10/2008 | Iobbi |
| 2009/0005863 A1 | 1/2009 | Goetz et al. |
| 2009/0012600 A1 | 1/2009 | Styrc et al. |
| 2009/0018570 A1 | 1/2009 | Righini et al. |
| 2009/0048656 A1 | 2/2009 | Wen |
| 2009/0054976 A1 | 2/2009 | Tuval et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0082858 A1 | 3/2009 | Nugent et al. |
| 2009/0085900 A1 | 4/2009 | Weiner |
| 2009/0099653 A1 | 4/2009 | Suri et al. |
| 2009/0138079 A1 | 5/2009 | Tuval et al. |
| 2009/0157175 A1 | 6/2009 | Benichou et al. |
| 2009/0164004 A1 | 6/2009 | Cohn |
| 2009/0164006 A1 | 6/2009 | Seguin et al. |
| 2009/0171447 A1 | 7/2009 | VonSegesser et al. |
| 2009/0171456 A1 | 7/2009 | Kveen et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0198316 A1 | 8/2009 | Laske et al. |
| 2009/0209955 A1 | 8/2009 | Forster et al. |
| 2009/0210052 A1 | 8/2009 | Forster et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0222082 A1 | 9/2009 | Lock et al. |
| 2009/0222084 A1 | 9/2009 | Friedman |
| 2009/0234443 A1 | 9/2009 | Ottma et al. |
| 2009/0240264 A1 | 9/2009 | Tuval et al. |
| 2009/0240320 A1 | 9/2009 | Tuval |
| 2009/0254165 A1 | 10/2009 | Tabor et al. |
| 2009/0287296 A1 | 11/2009 | Manasse |
| 2009/0287299 A1 | 11/2009 | Tabor et al. |
| 2010/0004740 A1 | 1/2010 | Seguin et al. |
| 2010/0030328 A1 | 2/2010 | Seguin et al. |
| 2010/0036479 A1 | 2/2010 | Hill et al. |
| 2010/0036485 A1 | 2/2010 | Seguin |
| 2010/0069852 A1 | 3/2010 | Kelley |
| 2010/0094411 A1 | 4/2010 | Tuval et al. |
| 2010/0100167 A1 | 4/2010 | Bortlein et al. |
| 2010/0131054 A1 | 5/2010 | Tuval et al. |
| 2010/0137979 A1 | 6/2010 | Tuval et al. |
| 2010/0145439 A1 | 6/2010 | Seguin et al. |
| 2010/0152840 A1 | 6/2010 | Seguin et al. |
| 2010/0161045 A1 | 6/2010 | Righini |
| 2010/0198346 A1 | 8/2010 | Keogh et al. |
| 2010/0234940 A1 | 9/2010 | Dolan |
| 2010/0256723 A1 | 10/2010 | Murray |
| 2010/0274351 A1 | 10/2010 | Rolando et al. |
| 2010/0292782 A1 | 11/2010 | Giannetti et al. |
| 2011/0082539 A1 | 4/2011 | Suri |
| 2011/0288636 A1 | 11/2011 | Rolando et al. |
| 2012/0172982 A1 | 7/2012 | Stacchino et al. |
| 2013/0325112 A1 | 12/2013 | Stacchino et al. |
| 2013/0345800 A1 | 12/2013 | Stacchino et al. |

FOREIGN PATENT DOCUMENTS

| | | |
|---|---|---|
| DE | 19532846 | 3/1997 |
| DE | 19546692 | 6/1997 |

(56) References Cited

FOREIGN PATENT DOCUMENTS

| | | |
|---|---|---|
| DE | 19907646 | 8/2000 |
| DE | 10010074 | 10/2001 |
| DE | 10049812 | 4/2002 |
| DE | 10049813 | 4/2002 |
| DE | 10049815 | 4/2002 |
| DE | 10121210 | 11/2002 |
| DE | 10301026 | 2/2004 |
| DE | 19857887 | 5/2005 |
| EP | 0133420 B1 | 2/1988 |
| EP | 0155245 B1 | 5/1990 |
| EP | 0592410 B1 | 10/1995 |
| EP | 0515324 B1 | 12/1996 |
| EP | 0850607 A1 | 7/1998 |
| EP | 1057460 A1 | 12/2000 |
| EP | 1255510 | 11/2002 |
| EP | 1259194 B1 | 2/2005 |
| EP | 1214020 B1 | 3/2005 |
| EP | 2055266 A2 | 5/2005 |
| EP | 1088529 B1 | 6/2005 |
| EP | 1570809 A1 | 9/2005 |
| EP | 1014896 B1 | 11/2005 |
| EP | 1469797 | 11/2005 |
| EP | 1603493 A2 | 12/2005 |
| EP | 1600127 B1 | 11/2006 |
| EP | 1143882 B1 | 5/2007 |
| EP | 2047824 | 4/2009 |
| EP | 1370201 B1 | 9/2009 |
| EP | 2119417 | 11/2009 |
| EP | 2133039 A1 | 12/2009 |
| FR | 2788217 | 12/1999 |
| FR | 2815844 | 5/2000 |
| GB | 2056023 | 3/1981 |
| NL | 1017275 | 8/2002 |
| WO | WO9529640 | 11/1995 |
| WO | WO9724989 A1 | 7/1997 |
| WO | WO9817202 A1 | 4/1998 |
| WO | WO9829057 A1 | 7/1998 |
| WO | WO9913802 A1 | 3/1999 |
| WO | WO9956665 A1 | 11/1999 |
| WO | WO0041652 A1 | 7/2000 |
| WO | WO0044313 | 8/2000 |
| WO | WO0047136 | 8/2000 |
| WO | WO0062714 A1 | 10/2000 |
| WO | WO0062716 A1 | 10/2000 |
| WO | WO0121107 A1 | 3/2001 |
| WO | WO0135870 | 5/2001 |
| WO | WO0149213 | 7/2001 |
| WO | WO0154625 | 8/2001 |
| WO | WO0162189 A1 | 8/2001 |
| WO | WO0047139 A1 | 9/2001 |
| WO | WO0164137 A1 | 9/2001 |
| WO | WO0176510 A2 | 10/2001 |
| WO | WO0222054 | 3/2002 |
| WO | WO0236048 | 5/2002 |
| WO | WO02041789 A3 | 8/2002 |
| WO | WO02076348 A1 | 10/2002 |
| WO | WO02047575 A3 | 12/2002 |
| WO | WO03011195 | 2/2003 |
| WO | WO03003943 A3 | 11/2003 |
| WO | WO03094797 A1 | 11/2003 |
| WO | WO03003949 A3 | 1/2004 |
| WO | WO2004019825 | 3/2004 |
| WO | WO2004082527 A2 | 9/2004 |
| WO | WO2004089250 | 10/2004 |
| WO | WO2005004753 | 1/2005 |
| WO | WO2004091455 A3 | 2/2005 |
| WO | WO2005046528 A1 | 5/2005 |
| WO | WO2006005015 A2 | 1/2006 |
| WO | WO2006026371 | 3/2006 |
| WO | WO2006044679 A1 | 4/2006 |
| WO | WO2006086135 A | 8/2006 |
| WO | WO2006093795 A1 | 9/2006 |
| WO | WO2007053243 A2 | 5/2007 |
| WO | WO2008028569 A1 | 3/2008 |
| WO | WO2008035337 A2 | 3/2008 |
| WO | WO2008047354 | 4/2008 |
| WO | WO2008138584 | 11/2008 |
| WO | WO2008150529 | 12/2008 |
| WO | WO2009002548 | 12/2008 |
| WO | WO2009024716 | 2/2009 |
| WO | WO2009029199 A1 | 3/2009 |
| WO | WO2009042196 | 4/2009 |
| WO | WO2009045331 | 4/2009 |
| WO | WO2009045338 | 4/2009 |
| WO | WO2009061389 | 5/2009 |
| WO | WO2009091509 | 7/2009 |
| WO | WO2009094188 | 7/2009 |
| WO | WO2009111241 | 9/2009 |

OTHER PUBLICATIONS

European Search Report issued in EP 10183557, mailed Apr. 11, 2011, 7 pages.

Andersen, H.R. et al, "Transluminal implantation of artificial heart valves. Description of a new expandable aortic valve and initial results with implantation by catheter technique in closed chest pigs." Euro. Heart J. (1992) 13:704-708.

Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.

Bailey, "Percutaneous Expandable Prosthetic Valves," In: Topol EJ, ed. Textbook of Interventional Cardiology. Volume II. Second edition. WB Saunders, Philadelphia, 1994:1268-1276.

Block, et al., "Percutaneous Approaches to Valvular Heart Disease," Current Cardiology Reports, vol. 7 (2005) pp. 108-113.

Bonhoeffer, et al, "Percutaneous Insertion of the Pulmonary Valve," Journal of the American College of Cardiology (United States), May 15, 2002, pp. I664-I669.

Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.

Bonhoeffer, et al, "Transcatheter Implantation of a Bovine Valve in Pulmonary Position: A Lamb Study," Circulation (United States), Aug. 15, 2000, pp. 813-816.

Boudjemline, et al, "Images in Cardiovascular Medicine. Percutaneous Aortic Valve Replacement in Animals," Circulation (United States), Mar. 16, 2004, 109, p. e I 61.

Boudjemline, et al, "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-BR66.

Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.

Boudjemline, et al, "Percutaneous Aortic Valve Replacement: Will We Get There?" Heart (British Cardiac Society) (England), Dec. 2001, pp. 705-706.

Boudjemline, et al, "Percutaneous Implantation of a Biological Valve in Aortic Position: Preliminary Results in a Sheep Study," European Heart Journal 22, Sep. 2001, p. 630.

Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.

Boudjemline, et al, "Percutaneous Implantation of a Valve in the Descending Aorta in Lambs," European Heart Journal (England), Jul. 2002, pp. 1045-1049.

Boudjemline, et al, "Percutaneous Pulmonary Valve Replacement in a Large Right Ventricular Outflow Tract: An Experimental Study," Journal of the American College of Cardiology (United States), Mar. 17, 2004, p. 1082-1087.

Boudjemline, et al, "Percutaneous Valve Insertion: A New Approach," Journal of Thoracic and Cardiovascular Surgery (United States), Mar. 2003, pp. 741-742.

(56) References Cited

OTHER PUBLICATIONS

Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.
Boudjemline, et al, "Steps Toward Percutaneous Aortic Valve Replacement," Circulation (United States), Feb. 12, 2002, pp. 775-778.
Boudjemline, et al, "The Percutaneous Implantable Heart Valve," Progress in Pediatric Cardiology (Ireland), 2001, pp. 89-93.
Boudjemline, et al, "Transcatheter Reconstruction of the Right Heart," Cardiology in the Young (England), Jun. 2003, pp. 308-311.
Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.
Cribier, A. et al, "Percutaneous Transcatheter Implantation of an Aortic Valve Prosthesis for Calcific Aortic Stenosis: First Human Case Description," Circulation (2002) 3006-3008.
Davidson et al., "Percutaneous therapies for valvular heart disease," Cardiovascular Pathology 15 (2006) 123-129.
European Search Report issued in EP App No. 08165227, dated Mar. 13, 2009.
European Search Report issued in EP App No. 09158822, dated Sep. 29, 2009, 5 pages.
European Search Report issued in EP Application No. 06101425, dated May 3, 2006, 6 pages.
European Search Report issued in EP Application No. 08150075, dated Mar. 27, 2008, 6 pages.
Extended European Search Report issued in EP 09179414, dated Oct. 18, 2010, 8 pages.
Henzel, et al., "Complications of percutaneous aortic valve replacement: experience with the CriberEdwardsTm percutaneous heart valve," EuroIntervention Supplements (2006), I (Supplement A) A3-A8.
Huber, et al., "Do Valved Stents Compromise Coronary Flow?" Eur. J. Cardiothorac. Surg. 2004;25:754-759.
International Search Report issued in International Application No. PCT/IB2006/000967, published as WO2006/085225, mailed Jul. 6, 2006.
Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.
Khambadkone, et al, "Percutaneous Implantation of Pulmonary Valves," Expert Review of Cardiovascular Therapy (England), Nov. 2003, pp. 541-548.
Khambadkone, et al, "Percutaneous Pulmonary Valve Implantation: Early and Medium Term Results," Circulation 108 (17 Supplement), Oct. 28, 2003, p. 1V-375.
Khambadkone, et al, "Percutaneous Pulmonary Valve Implantation: Impact of Morphology on Case Selection," Circulation 108 (17 Supplement), Oct. 28, 2003, p. IV-642-IV-643.
Lutter, et al, "Percutaneous Aortic Valve Replacement: An Experimental Study. I. Studies on Implantation," The Journal of Thoracic and Cardiovascular Surgery, Apr. 2002, pp. 768-776.
Lutter, et al, "Percutaneous Valve Replacement: Current State and Future Prospects," Annals of Thoracic Surgery (Netherlands), Dec. 2004, pp. 2199-206.
Ma, Ling, et al., "Double-crowned valved stents for off-pump mitrel valve replacement," European Journal of Cardio Thoracic Surgery, 28:194-198, 2005.
Medtech Insight, "New Frontiers in Heart Valve Disease," vol. 7, No. 8 (2005).
Palacios, "Percutaneous Valve Replacement and Repair, Fiction or Reality?" Journal of American College of Cardiology, vol. 44, No. 8 (2004) pp. 1662-1663.
Pavcnik et al., "Aortic and venous valve for percutaneous insertion," Min. Invas. Ther. & Allied Techol. 2000, vol. 9, pp. 287-292.
Pelton et al., "Medical Uses of Nitinol," Materials Science Forum vols. 327-328, pp. 63-70 (2000).
Ruiz, "Transcathether Aortic Valve Implantation and Mitral Valve Repair: State of the Art," Pediatric Cardiology, vol. 26, No. 3 (2005).
Saliba, et al, "Treatment of Obstructions of Prosthetic Conduits by Percutaneous Implantation of Stents," Archives des Maldies du Coeur et des Vaisseaux (France), 1999, pp. 591-596.
Stassano et al., "Mid-term results of the valve-on-valve technique for bioprosthetic failure," Eur. J. Cardiothorac. Surg. 2000; 18:453-457.
Webb, et al., "Percutaneous Aortic Valve Implantation Retrograde from the Femoral Artery," Circulation (2006), 1 13;842-850.
Definition of Hinge downloaded from Voculabulary.com, received at the EPO on Dec. 18, 2012, 1 page.
Definition of Hinge, downloaded from www.meriam-webster.com on Jan. 31, 2013, 3 pages.
Definition of Minimum, downloaded from www.meriam-webster.com on Jan. 31, 2013, 2 pages.
European Search Report issued in EP Application No. 11425029, dated Aug. 17, 2011, 5 pages.
European Search Report issued in EP Application No. 11425030, dated Aug. 10, 2011, 5 pages.
International Search Report and Written Opinion issued in PCT/IB2012/050604, mailed Jul. 26, 2012, 16 pages.
International Search Report and Written Opinion issued in PCT/IB2012/050608, mailed Jul. 24, 2012, 9 pages.
Roth, Mark, "Old metal heart valve did its job for 42 years", Pittsburgh Post-Gazette, Wednesday Mar. 5, 2008, 3 pages.

\* cited by examiner

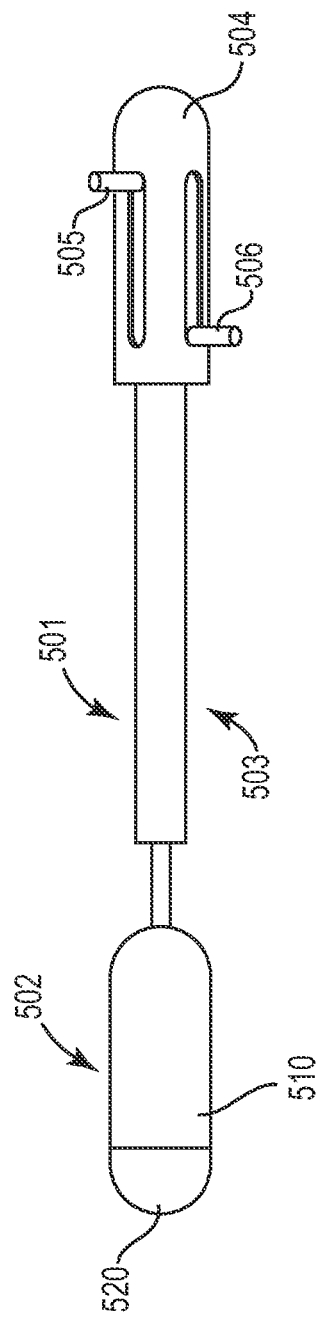
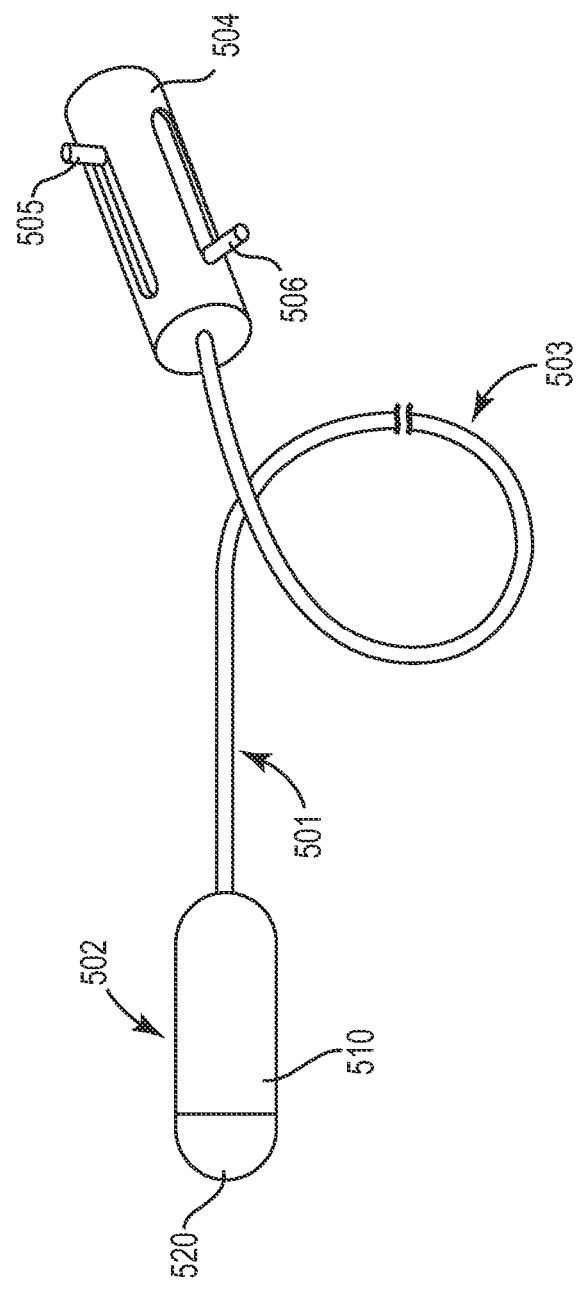

MINIMALLY INVASIVE AORTIC VALVE REPLACEMENT

CROSS-REFERENCE TO RELATED APPLICATIONS

This application claims the benefit of U.S. Patent Application Ser. No. 61/248,742 filed Oct. 5, 2009 entitled "MINIMALLY INVASIVE AORTIC VALVE REPLACEMENT," which application is hereby incorporated by reference herein in its entirety.

TECHNICAL FIELD

The disclosure pertains generally to valve replacement procedures and more particularly to minimally invasive valve replacement procedures.

BACKGROUND

Natural heart valves, such as aortic valves, mitral valves, pulmonary valves, and tricuspid valves, often become damaged by disease in such a manner that they fail to maintain bodily fluid flow in a single direction. A malfunctioning heart valve may be stenotic (i.e., calcification of the valve leaflets) or regurgitant (i.e., heart leaflets are wide open). Maintenance of blood flow in a single direction through the heart valve is important for proper flow, pressure, and perfusion of blood through the body. Hence, a heart valve that does not function properly may noticeably impair the function of the heart. Left untreated, coronary valve disease can lead to death. There has been increasing consideration given to the possibility of using, as an alternative to traditional cardiac-valve prostheses, valves designed to be implanted using minimally-invasive surgical techniques or endovascular delivery (so-called "percutaneous valves").

SUMMARY

Example 1 is a minimally invasive method of implanting a prosthetic aortic valve that includes forming a surgical site within a patient's chest that includes a first access port, a second access port, a viewing port and a delivery port. A camera is inserted into the viewing port. Each of the native aortic valve leaflets are grasped with a remotely operated tissue grasping device that is inserted into one of the first and second access ports. Each of the grasped native aortic valve leaflets are then excised with a remotely operated cutting device inserted into another of the first and second access ports. The prosthetic aortic valve is delivered through the delivery port to the valve annulus using a delivery device. The prosthetic aortic valve is implanted at the valve annulus and the delivery device is withdrawn. A surgeon performs the remotely operated steps while viewing images provided by the camera.

In Example 2, the method of Example 1, further including a step, prior to valve delivery, of suturing guide lines to tissue proximate the valve annulus.

In Example 3, the method of Example 2, further including a step, prior to valve delivery, of attaching the guide lines to the self-expanding prosthetic aortic valve to rotationally locate the self-expanding prosthetic aortic valve relative to the valve annulus.

In Example 4, the method of any of Examples 1-3, further including a step, after inserting the camera, of remotely transecting the patient's aorta to gain access to the native aortic valve.

In Example 5, the method of Example 4 in which the step of remotely transecting the patient's aorta includes cutting the aorta with the remotely operated cutting device.

In Example 6, the method of any of Examples 1-5, further including a step, subsequent to withdrawing the delivery device, of remotely suturing the transected aorta.

In Example 7, the method of any of Examples 1-6 in which the step of implanting the self-expanding prosthetic aortic valve using the delivery device includes using the delivery device to position and subsequently expand the self-expanding prosthetic aortic valve.

In Example 8, the method of any of Examples 1-7 in which the surgeon performs the remotely operated steps by manipulating a control device that translates the surgeon's hand movements into operational commands for the remotely operated devices.

In Example 9, the method of Example 8 in which the control device also scales the surgeon's hand movements.

Example 10 is a method in which a patient's native aortic valve is robotically replaced with a prosthetic aortic valve by operating one or more master input devices that provide commands to a plurality of slave tools. Access is provided to the native aortic valve having a valve annulus. Each of the native aortic valve leaflets are grasped with one of the plurality of slave tools and are excised with another of the plurality of slave tools. The prosthetic valve is implanted at the valve annulus.

In Example 11, the method of Example 10 in which the step of providing access to the native aortic valve includes performing an aortotomy with another of the plurality of slave tools.

In Example 12, the method of either Example 10 or Example 11 in which a surgeon operates the one or more master input devices while viewing the surgical site via displayed images provided by a camera disposed within the surgical site.

In Example 13, the method of any of Examples 10-12 in which movement of the one or more master input devices are translated into commands for the plurality of slave tools.

In Example 14, the method of any of Examples 10-13 in which the step of implanting the self-expanding prosthetic aortic valve with another of the plurality of slave tools includes implanting the self-expanding prosthetic aortic valve with a slave tool that is configured to hold the self-expanding prosthetic aortic valve in a collapsed position for delivery and subsequently permit expansion of the self-expanding prosthetic aortic valve.

Example 15 is a minimally invasive method of performing an aortic valve replacement procedure that includes establishing surgical access including a working port, a delivery port and a viewing port. A camera is inserted through the viewing port. The valve leaflets are removed using a removal device inserted through the working port. At least one suture is attached at the valve annulus at a location near a center of a Valsalva sinus. A prosthetic valve is delivered over the suture, the prosthetic valve having a protrusion that is adapted to conform to the Valsalva sinus. The prosthetic valve is implanted at the valve annulus such that the protrusion is located in the Valsalva sinus.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE FIGURES

FIGS. 5A and 5B are schematic illustrations of an embodiment of a delivery device.

Figure 1:
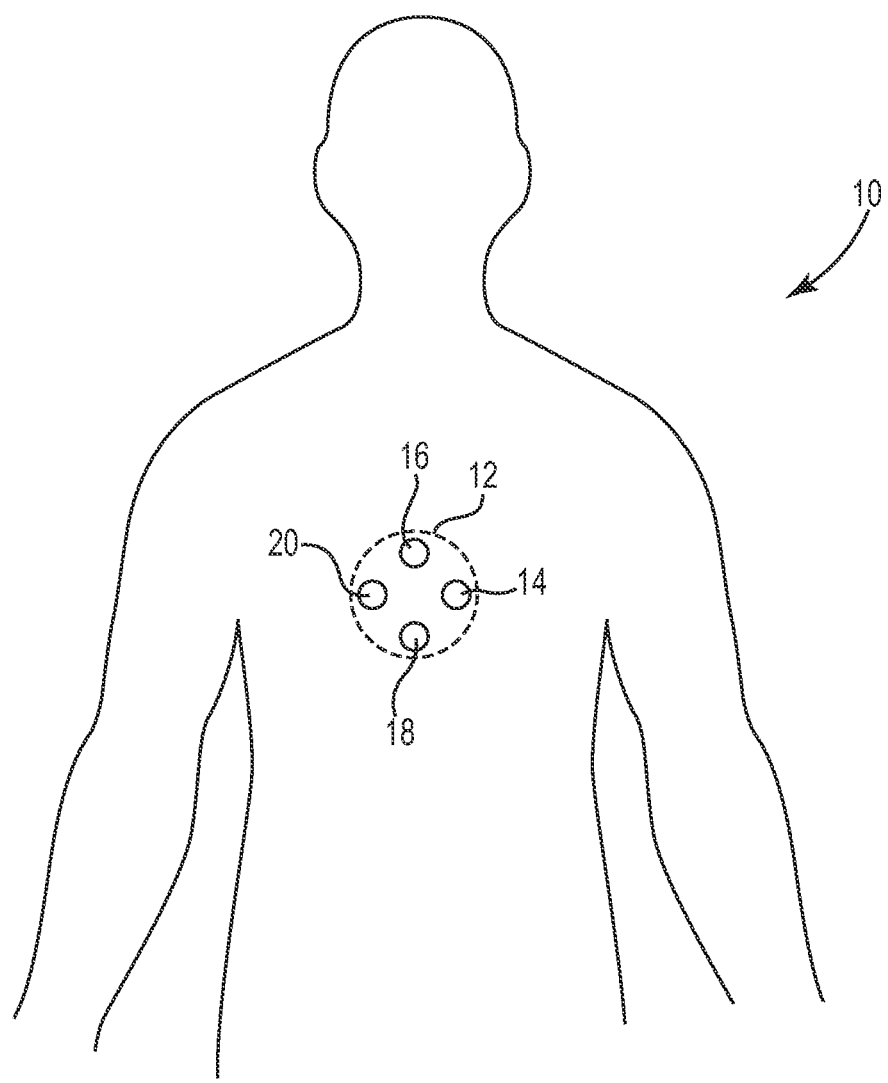
FIG. 1 is a schematic view of a patient illustrating the placement of minimally invasive access.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

A variety of surgical procedures may be improved using minimally invasive techniques. In a minimally invasive thoracic procedure, for example, one or more access ports may be formed within an operating region in a patient's chest. In some embodiments, a camera or other imaging apparatus may be inserted through one of the access ports to provide the surgeon with a highly detailed view of the surgical site. In some embodiments, surgical procedures such as cutting, suturing and device implantation may be accomplished through one or more of the access ports.

FIG. 1 is a schematic illustration of a patient 10 who is undergoing or is about to undergo a minimally invasive thoracic procedure. In this particular embodiment, the patient 10 will be undergoing a minimally invasive aortic valve replacement procedure, but the techniques described herein may be applicable to other surgical procedures as well. In the illustrated embodiment, a total of four access ports have been formed within a surgical site 12. In other embodiments, more than four access ports may be used. In some cases, less than four access ports may be needed.

In the illustrated embodiment, the access ports include a viewing port 14 through which a camera or other viewing apparatus may be inserted. The access ports include a first cutting port 16 and a second cutting port 18. As will be discussed in greater detail with respect to subsequent Figures, a surgeon may use the first cutting port 16 and the second cutting port 18 to make appropriate incisions within the patient in order to gain access to particular areas, excise undesired tissue, and the like, using tools that can be inserted through the first cutting port 16 and/or the second cutting port 18. In this, the designations of first and second are arbitrary and are not intended to denote any order of use or importance. The access ports also include a delivery port 20. The delivery port 20 may be used, for example, to deliver a device to be implanted. In the illustrated embodiment, the delivery port 20 may be used to deliver an implantable valve prosthesis.

In some embodiments, the tools inserted through the first cutting port 16, the second cutting port 18 and/or the delivery port 20 may be inserted and controlled manually. For example, a camera inserted through the viewing port 14 may be connected to a display device (not illustrated) that can be used to display real-time images of the internal surgical site. The surgeon can use the real-time images to guide whatever tools have been inserted into the patient.

In some embodiments, however, minimally invasive procedures such as those discussed herein may be performed robotically. In a robotic or remote procedure, a surgeon may manipulate a set of controls while watching a televised image of the surgical site. The surgeon's movements may be translated to the tools discussed above. In some embodiments, the movements are modified to reduce or eliminate the effects of undesired hand movement. In some cases, the movements are scaled, i.e., for a given movement by the surgeon, the appropriate tool moves a distance that is a particular fraction of the distance the surgeon moves. In some embodiments, scaling the movement provides advantages in accuracy, particularly when working on small or delicate anatomical features.

Figure 2:
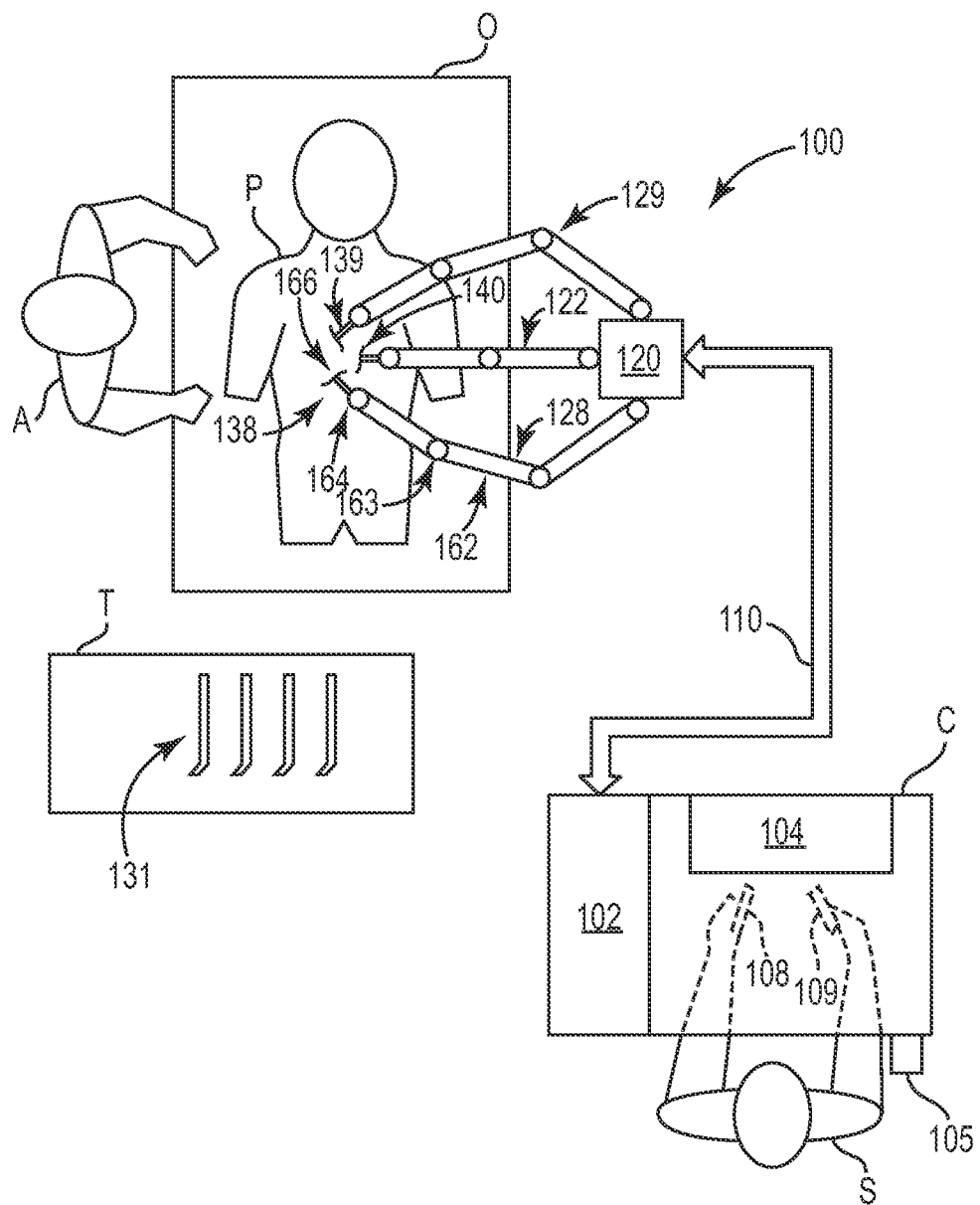
FIG. 2 is a schematic view of an embodiment of a remote surgical system.

FIG. 2 is a schematic illustration of a robotic system that is configured to assist a surgeon in performing minimally invasive procedures such as a minimally invasive aortic valve replacement procedure. In FIG. 2, the system 100 includes a console C utilized by a surgeon S. One or more assistants A may assist the surgeon S while performing a medical procedure on a patient P who is disposed on an operating table O. In some embodiments, the console C includes a three dimensional monitor 104 that is configured to display a three-dimensional image of a surgical site.

The console C also includes a number of manipulative control devices. As illustrated, the console C includes a left control device 108, a right control device 109, a foot pedal 105 and a processor 102. In some embodiments, the control devices 108, 109 may include any one or more of a variety of input devices such as joysticks, gloves, trigger-guns, hand-operated controllers, or the like. The processor 102 may be a dedicated computer integrated into the Console C or positioned next or near to it, or it may be broken up into a number of processing or controller components that are distributed in a distributed processing fashion throughout the system 100.

The surgeon S performs a medical procedure by manipulating the control devices 108, 109 (also referred to herein as "master manipulators" and "master input devices") so that the processor 102 causes slave manipulators of their respectively associated robotic arm assemblies 128, 129 to manipulate their respective removably coupled surgical instruments 138, 139 (also referred to herein as "tools") accordingly, while the surgeon S views the surgical site in 3-D on the console monitor 104 as it is captured by a stereoscopic camera 140.

Each of the tools 138, 139, as well as the camera 140, is conventionally inserted through a tool guide (not shown) into the patient P so as to extend down to the surgical site through a corresponding minimally invasive incision such as an incision 166. The number of surgical tools used at one time and consequently, the number of robotic arms being used in the system 100 will generally depend on the medical procedure being performed and the space constraints within the operating room, among other factors. If it is necessary to change a tool being used during a procedure, the assistant A may remove the tool no longer being used from its robotic arm assembly, and replace it with another tool 131 from a tray T in the operating room.

So that the tools 138, 139 may be manipulated at the surgical site, they may each have a wrist mechanism including three joints (or other drivable mechanical elements such as gears, spools, etc.) for controlling the orientation of the wrist mechanism, and an additional joint (or other drivable mechanical element) controlling the eventual grip or other end effector joint of the tool. In some embodiments, suitable tool wrists and end effector mechanisms (and the mechanical elements and other linkages driving them), are described, e.g., U.S. Pat. No. 6,676,684 "Roll-Pitch-Roll-Yaw Surgical Tool", which is incorporated herein by reference.

Each of the robotic arm assemblies 122, 128, 129 includes a slave manipulator and setup arms. The slave manipulators are robotically moved using motor controlled joints (also referred to herein as "active joints") in order to manipulate and/or move their respectively held medical devices. The setup arms may be manually manipulated by releasing normally braked joints (also referred to herein as "setup joints") to horizontally and vertically position the robotic arm assemblies 122, 128, 129 so that their respective medical devices may be inserted into their respective tool guides.

In some embodiments, the monitor 104 is positioned near the surgeon's S hands so that it will display a projected image that is oriented so that the surgeon S feels that he or she is actually looking directly down onto the operating site. To that end, images of the tools 138, 139 preferably appear to be located substantially where the surgeon's S hands are located.

The processor 102 performs various functions in the system 100. One important function that it performs is to translate and transfer the mechanical motion of control devices 108, 109 to their respective slave manipulators of robotic arm assemblies 128, 129 through control signals over bus 110 so that the surgeon S can effectively manipulate their respective tools 138, 139. Another important function is to implement various control system processes as described herein. Although described as a processor, it is to be appreciated that the processor 102 may be implemented in practice by any combination of hardware, software and firmware. Also, its functions as described herein may be performed by one unit, or divided up among different components, each of which may be implemented in turn by any combination of hardware, software and firmware.

In some embodiments, suitable medical robotic systems are described, for example, in U.S. Pat. Nos. 6,493,608; 6,424,885 and 7,453,227, each of which are incorporated herein by reference in their entirety. Illustrative but non-limiting examples of medical robotic systems include those available from Intuitive Surgical, Inc., of Sunnyvale Calif. under the da Vinci tradename.

Figure 3:
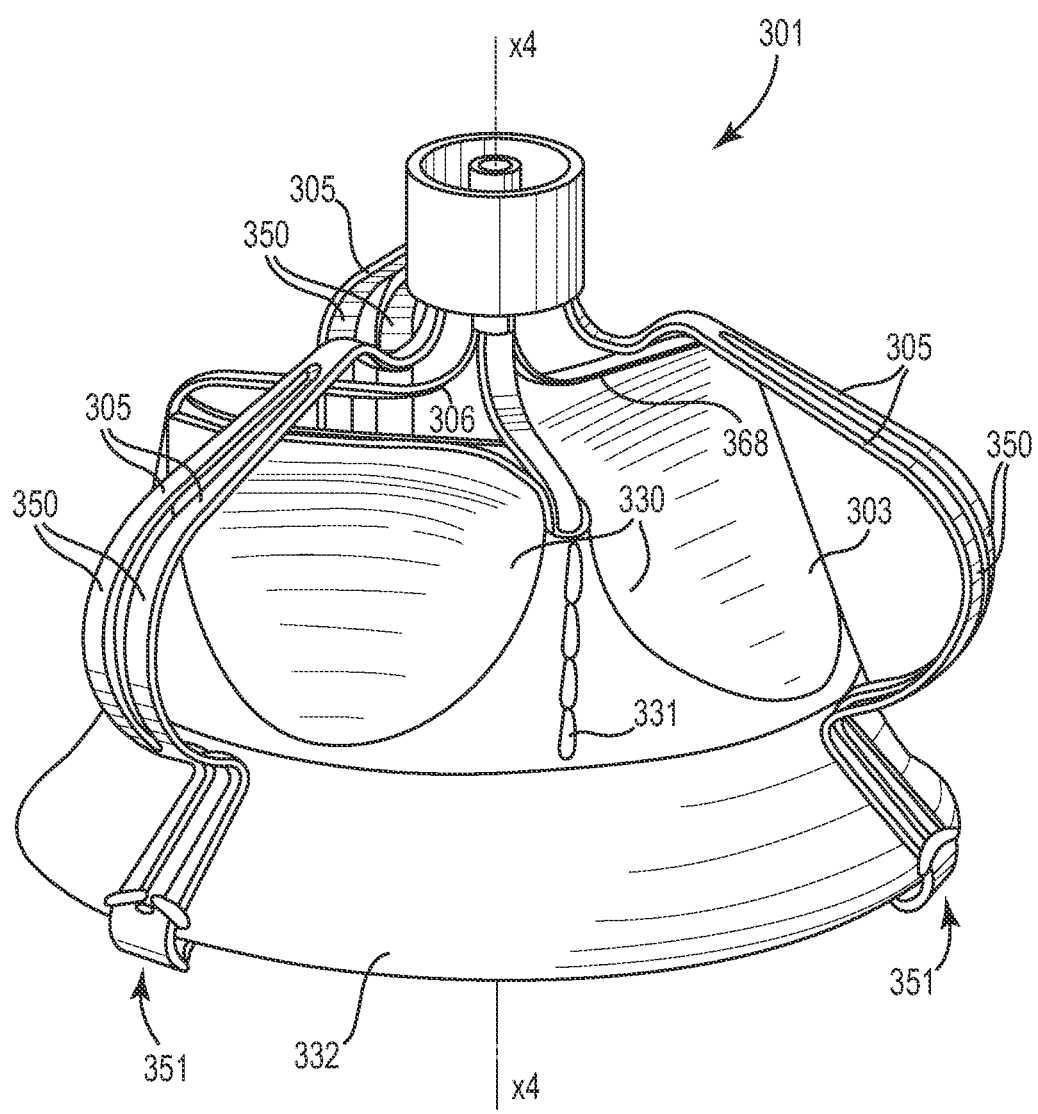
FIG. 3 is a perspective view of an embodiment of an implantable prosthetic aortic valve.

A variety of different valves, including prosthetic aortic valves, may be implanted using the minimally invasive procedures discussed herein. An illustrative but non-limiting example of a suitable prosthetic valve may be seen in FIG. 3. FIG. 3 illustrates a valve 301 that can be implanted in a variety of ways, including a minimally invasive procedure. The valve 301 includes an armature 302 and a set of leaflets 303. The armature 302 has a general cage-like structure that includes a number of ribs extending along an axis X4. The ribs include a first series of ribs 305 and a second series of ribs 306. The ribs 305, 306 may be made of a radially expandable metal. In some embodiments, the ribs 305, 306 may be formed of a shape memory material such as Nitinol.

The first series of ribs 305 and the second series of ribs 306 have different functions. In some embodiments, the ribs 305 form an external or anchor portion of the armature 302 that is configured to enable the location and anchorage of the valve 301 at an implantation site. The ribs 306 are configured to provide an internal or support portion of the armature 302. In some embodiments, the ribs 306 support a plurality of valve leaflets 330 provided within the set of leaflets 303.

In some embodiments, the ribs 305 are arranged in sets of ribs (threes or multiples of three) such that they are more readily adaptable, in a complementary way, to the anatomy of the Valsalva's sinuses, which is the site of choice for implantation of the valve 301. The Valsalva's sinuses are the dilatations, from the overall lobed profile, which are present at the root of the aorta, hence in a physiologically distal position with respect to the aortic valve annulus.

In some embodiments, the structure and the configuration of the ribs 306 is, as a whole, akin to that of the ribs 305. In the case of the ribs 306, which form the internal part of the armature 302 of the valve 301, there is, however, usually the presence of just three elements that support, in a position corresponding to homologous lines of commissure (which take material form as sutures 331), on the valve leaflets 330. Essentially, the complex of ribs 306 and valve leaflets 330 is designed to form the normal structure of a biological valve prosthesis. This is a valve prosthesis which (in the form that is to be implanted with a surgical operation of a traditional type, hence of an invasive nature) has met with a wide popularity in the art.

In some embodiments, suitable materials used to form the leaflets 330, such as the pericardium or meningeal tissue of animal origin are described for example in EP 0 155 245 B and EP 0 133 420 B, both of which are hereby incorporated by reference herein in their entirety. In some embodiments, the valve 301 may be similar to those described in U.S. Patent Publication No. 2005/0197695, which is hereby incorporated by reference herein in its entirety.

Figure 4:
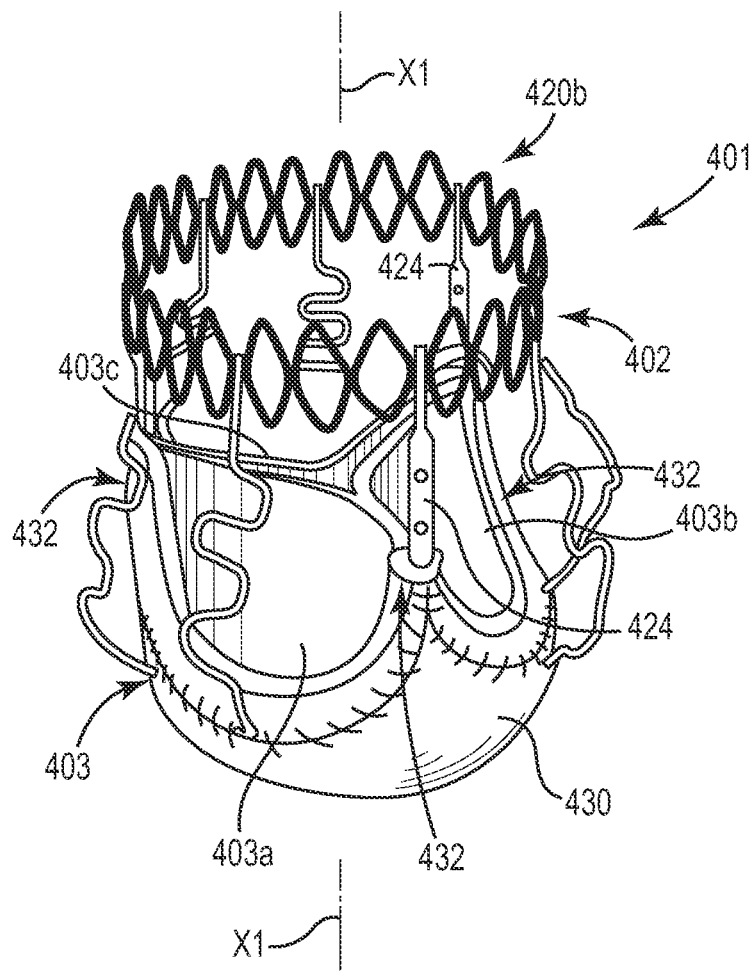
FIG. 4 is a perspective view of an embodiment of an implantable prosthetic aortic valve.

Another illustrative but non-limiting example of a suitable prosthetic valve may be seen in FIG. 4. FIG. 4 illustrates a prosthetic valve 401 that can be implanted using a variety of different techniques. In some embodiments, the valve 401 may be implanted using a minimally invasive procedure such as those discussed herein. As illustrated, the valve 401 includes an armature 402 and a valve sleeve 403 that is coupled to the armature 402 and that includes three valve leaflets 403a, 403b and 403c.

As can be seen, the armature 402 has a general cage-like structure and is generally symmetric about a principal axis X1. As shown, the armature 402 defines a lumen which operates as a flow tube or duct to accommodate the flow of blood there through. As will be readily apparent to those skilled in the art, a major characteristic of the present invention is the absence of structural elements that can extend in the lumen through which blood flows.

The valve sleeve 403 may be constructed according to various techniques known in the art. For example, in some embodiments, techniques for the formation of the valve leaflets, assembly of the valve sleeve and installation thereof on an armature that can be used in the context of the present disclosure are described in EP-A-0 133 420, EP-A-0 155 245 and EP-A-0 515 324 (all of which are hereby incorporated by reference). In some embodiments, the valve 401 may be similar to those described in U.S. Patent Publication No. 2006/0178740, which is hereby incorporated by reference herein in its entirety.

As will be understood by those of ordinary skill in the art, in operation, the valve leaflets 403a, 403b, 403c are able to undergo deformation, divaricating and moving up against the armature 402 so as to enable free flow of the blood through the prosthesis. When the pressure gradient, and hence the direction of flow, of the blood through the prosthesis tends to be reversed, the valve leaflets 403a, 403b, 403c then move into the position represented in FIG. 4, in which they substantially prevent the flow of the blood through the prosthesis. In some embodiments, the valve leaflets 403a, 403b, 403c are made in such a way as to assume spontaneously, in the absence of external stresses, the closed configuration represented in FIG. 4.

The prosthetic valves described herein, such as the valve 301 and the valve 401, may be delivered in a variety of different manners. In some embodiments, a prosthetic valve may be delivered in a minimally invasive manner in which the valve is disposed on a delivery apparatus that is configured to be inserted into the patient through a minimally invasive incision (such as the access ports discussed above with respect to FIG. 1). Once the prosthetic valve has been appropriately positioned, the delivery apparatus can be manipulated to deploy the valve.

An illustrative but non-limiting example of a suitable delivery device that can be used manually or via the robotic system 100 (of FIG. 2) can be seen in FIGS. 5A and 5B, which are schematic illustrations of a delivery device 501. In some embodiments, the delivery device is manually operated by the surgeon S or by a second physician (not illustrated). In the illustrated embodiment, the delivery device 501 includes a carrier portion 502 for enclosing and carrying a prosthetic device (not visible in this view) and a manipulation portion 503 that couples the carrier portion 502 to a control handle 504. The control handle 504 includes several actuator members such as the sliders 505 and 506. In some embodiments, an optional third actuator member may be provided for controlling translational movement of the carrier portion 502 relative to the control handle 504. As will be appreciated, this feature permits microadjustment of the carrier portion 502 and the valve prosthesis in relation to a desired location while the control handle 504 is in a fixed location. A further optional actuator on the control handle 504 provides rotational adjustment of carrier portion 502 in relation to manipulation portion 50503 and/or control handle 4. This permits the optional placement of the valve prosthesis through at least 360 degrees of rotation.

The manipulation portion 503 may have more than one configuration. FIG. 5A shows a configuration in which the manipulation portion 503 is a substantially rigid bar having a length that permits positioning of the carrier portion 503, and hence the prosthetic valve disposed therein, at an aortic valve site. In some embodiments, the substantially rigid bar may have a length of about 10 centimeters. The delivery device 501 is sized and dimensioned to permit easy surgical manipulation of the entire instruction as well as the actuators on the instrument without contacting parts of the subject in a way to interfere with the user's position of the valve prosthesis.

FIG. 5B illustrates an embodiment in which the manipulation portion 503 is an elongated, flexible catheter-like member that can be used for transvascular catherization. However, this embodiment can be used in the minimally invasive procedures discussed herein. In some embodiments, the catheter-like member is braided or is otherwise configured to facilitate torque transmission from the control handle 504 to the carrier portion 502 such that the operator may effect radial positioning of the carrier portion 502 during the implantation procedure.

Figure 6:
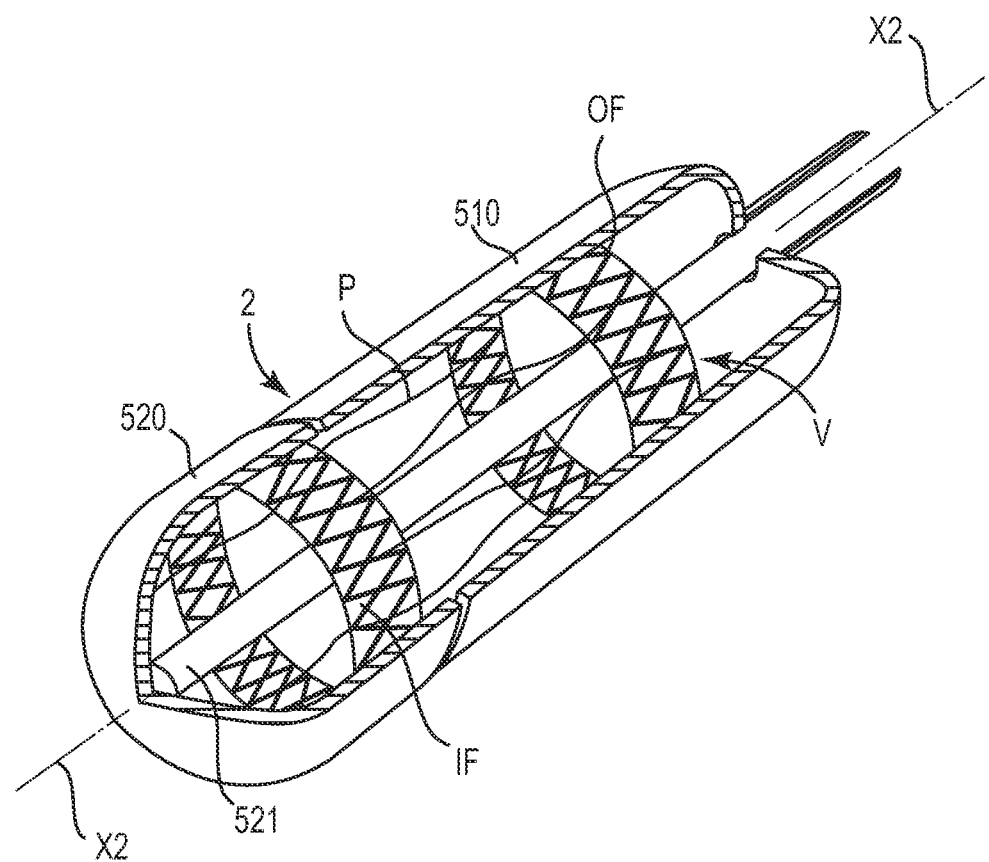
FIG. 6 is a partial cross-section of the delivery device shown in FIGS. 5A and 5B.

As shown in FIG. 6, the carrier portion 502 includes two deployment elements 510 and 520, each of which are independently operable to allow the expansion of at least one corresponding, radially expandable portion of the valve prosthesis V. In some embodiments, the valve prosthesis V may be self-expanding or may require expansion by another device (such as, for example, balloon expansion).

In the illustrated embodiment, the valve prosthesis V is self-expanding, and is arranged within the carrier portion 502 such that an expandable portion IF and an expandable portion OF are each located within one of the deployment elements 510, 520. Each deployment element 510, 520 may be formed as a collar, cap or sheath. In yet a further embodiment, the elements 510, 520 are porous (or have apertures) such that blood flow is facilitated prior, during and after placement of prosthesis V. As will be appreciated, blood flows through the elements 510, 520 and over or through the prosthesis V during the placement procedure. Each deployment element 510, 520 is able to constrain the portions IF, OF in a radially contracted position, against the elastic strength of its constituent material. The portions IF, OF are able to radially expand, as a result of their characteristics of superelasticity, only when released from the deployment element 510, 520. Typically, the release of the portions IF, OF is obtained by causing an axial movement of the deployment elements 510, 520 along the main axis X2 of the carrier portion 502. In one embodiment, the operator causes this axial movement by manipulating the sliders 505 and 506, which are coupled to the deployment elements 510, 520. In some embodiments, suitable delivery devices such as the delivery device 501 may be found in U.S. Patent Publication No. 2008/0147182, which is hereby incorporated by reference herein in its entirety.

Figure 7:
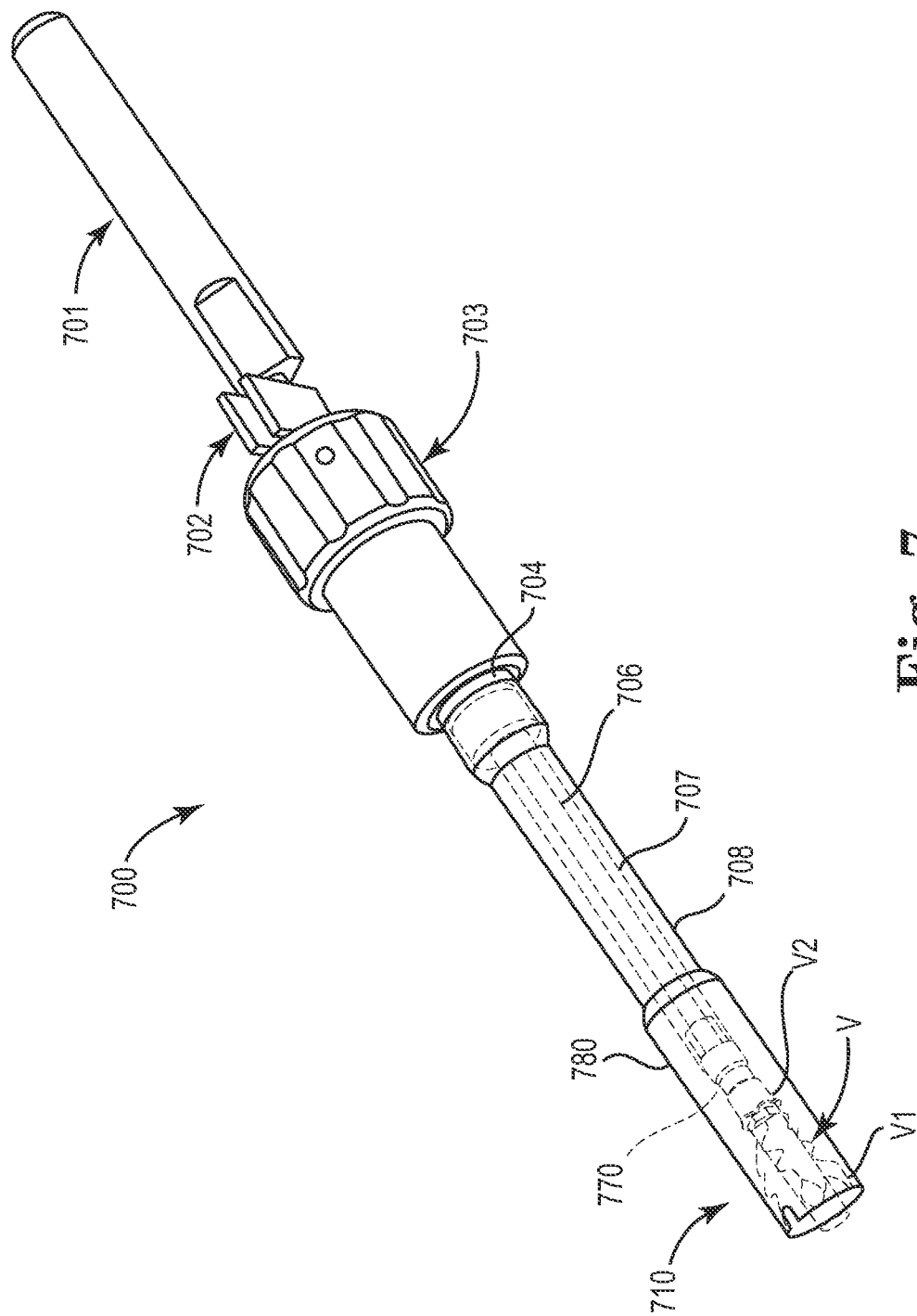
FIG. 7 is a schematic illustration of an embodiment of a delivery device.

Another illustrative but non-limiting example of a delivery device that may be manipulated manually or by the robotic system 100 (of FIG. 2) may be seen in FIG. 7. FIG. 7 shows an prosthetic valve delivery device 700 that includes a handle 701 for manipulation by a practitioner and a holder unit 710 for a valve V to be delivered. In the illustrated embodiment, the handle 701 and the holder unit 710 are generally located at proximal and distal ends, respectively, of the device 700. In this, proximal refers to the portion of the device 700 manipulated by the practitioner while distal refer to the end of the device 700 at which the valve V is delivered.

In one embodiment, the valve V includes two annular end portions V1 and V2 and is arranged within the holder unit 710 at the distal delivery end of the device 700 with the annular portions V1, V2 in a radially contracted configuration. In some embodiments, the valve V is delivered by releasing the annular portion V1 first and then by causing the valve V to gradually expand (e.g. due to its elastic or superelastic nature), starting from the portion V1 and continuing to the portion V2, until expansion is complete.

Figure 8:
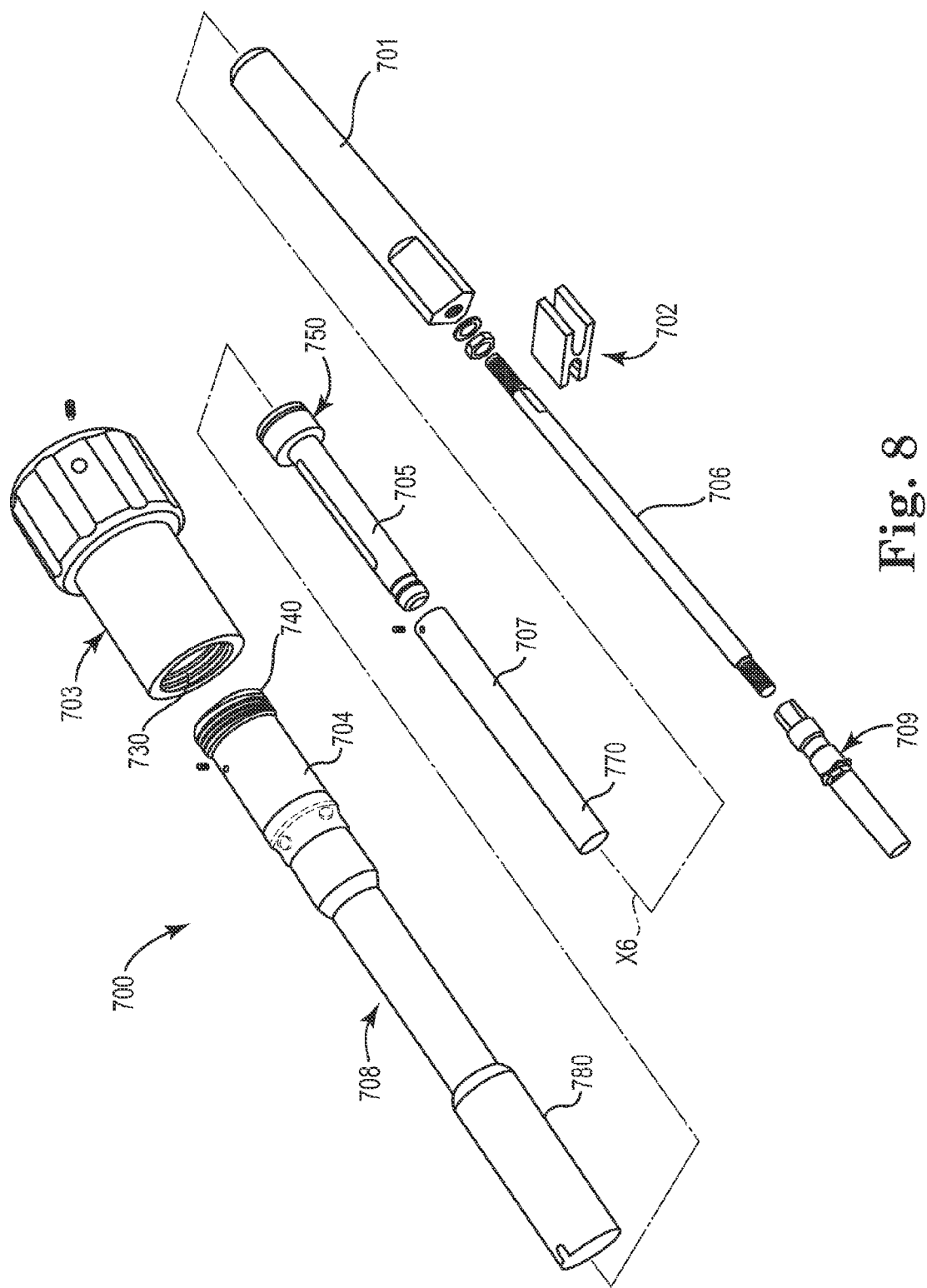
FIG. 8 is an exploded view of the delivery device of claim 7.

As shown in the exploded view of FIG. 8, a shaft 706 (which may be either rigid or flexible) extends from the handle 701 to the holder unit 710 for the valve. The holder unit 710 includes an annular groove or similar recessed 709 formation adapted to receive the (proximal) annular portion V2 of the valve V in a radially contracted condition. A tubular sheath or sleeve is slidably arranged over the shaft 706. Such a sleeve (hereinafter the "inner" sleeve) includes a proximal portion 705 proximate the handle 701 as well as a distal portion 707. The inner sleeve is of a length such that it can extend axially over the shaft 706 to form with its marginal end an intermediate tubular member 770 of the holder unit 710 which surrounds the formation 709 to radially constrain and retain the annular portion V2 of the valve V located therein.

In some embodiments, the proximal portion 705 of the inner sheet or sleeve terminates in an annular member 750 adapted to abut against a stop member 702. When in place on the shaft 706, the stop member 702 prevents the inner sleeve from being retracted (i.e. slid back) along the axis X6 of the shaft 706 from the position shown in FIG. 7, where the intermediate member or constraint 770 of the holder unit 710 radially constrains and retains the annular portion V2 of the valve V. When the stop member 702 is removed or otherwise disengaged, the inner sleeve can be retracted along the axis X6 so that the intermediate member 770 of the holder unit releases the annular portion V2 of the valve V.

In one embodiment, the stop or blocking member 702 includes a fork-shaped body (e.g. of plastics material) adapted to be arranged astride the root portion of the shaft 706 between the annular member 750 and the handle 701 to prevent "backward" movement of the inner sleeve towards the handle 701.

A further tubular sheet or sleeve (hereinafter the "outer" sleeve) is slidably arranged over the inner sleeve 705, 707. The outer sleeve 704 includes a proximal portion having an outer threaded surface 740 to cooperate with a complementary threaded formation 730 provided at the inner surface of a tubular rotary actuation member 703 arranged around the proximal portion 704 of the outer sleeves. In an embodiment, the actuation member 703 encloses the annular member 750 of the inner sleeve. The outer sleeve 704 extends over the inner sleeve 705, 707 and terminates with a distal portion 708 including an terminal constraint or outer member 780 adapted to extend around the distal portion to form an external tubular member of the holder unit 710 adapted to radially constrain and retain the annular portion V1 of the valve V located therein.

In some embodiments, the threaded surface/formations 730, 740 form a "micrometric" device actuatable by rotating the actuation member 703 to produce and precisely control axial displacement of the outer sleeve along the axis X6 of the shaft 706. Such a controlled movement may take place along the axis X6 of the shaft 706 starting from an extended position, as shown in FIG. 7, where the outer member 780 of the holder unit 710 radially constrains and retains the valve V. In these embodiments, which allow such a gradual movement or retraction, the outer member 780 gradually releases first the annular portion V1 of the valve V and then the remaining portions of the valve located between the annular portion V1 and the annular portion V2, thus permitting gradual radial expansion of the valve V.

In one embodiment, the retraction movement produced by the "micrometric" actuation device 730, 740 actuated via the rotary member 703 is stopped when the distal marginal end of the outer member 780 is aligned with the marginal end of the intermediate member 770 which still radially constrains and retains the annular portion V2 of the valve V in the formation 709. As further described below, in that condition, the valve V is partly expanded (i.e., more or less "basket-like") with the annular portion V1 completely (or almost completely) expanded and the annular portion V1 still contracted.

Starting from that position, if the stop member 702 is removed or otherwise disengaged, both the inner sleeve and the (retracted) outer sleeve mounted thereon can be slid back along the axis X6 towards the handle 701. In that way, the intermediate member 770 of the holder unit 710 releases the annular portion V2 of the valve V thus permitting valve expansion to become complete. Valve expansion is not hindered by the member 780 as this is likewise retracted towards the handle 701.

In an illustrative embodiment, the practitioner introduces the device 700 into the patient's body. In some embodiments, this is done in a minimally invasive manner, such as through one of the access ports described above with respect to FIG. 1. In a particular example of aortic valve replacement, the device 700 may be placed such that the outer member 780 is located immediately distal (with respect to blood flow from the left ventricle) of the aortic annuls so that the annular portions V1 and V2 are located on opposite sides of the Valsalva sinuses.

One the device 700 is placed such that the outer member 780 is disposed properly at the annulus site, the rotary actuation member 730 may be actuated by rotating the rotary actuation member in such a way that cooperation of the threaded sections 730 and 740 will cause the outer sleeve 704, 708 to start gradually retracting towards the handle 701. As a result of this retraction of the outer sleeve, the outer member 780 will gradually disengage the annular portion V1 of the valve V. The annular portion V1 will thus be allowed to radially expand.

Gradual withdrawal of the outer sleeve 704, 708 proceeds until the outer member 780 has almost completely disengaged the valve V, while the annular formation V2 is still securely retained by the intermediate member 770 of the inner sleeve 705, 707 which maintains the annular formation V2 of the valve on the holder portion 709. This deployment mechanism of the annular formation V1 and the valve V may be controlled very precisely by the practitioner via the screw-like mechanism 730, 740 actuated by the rotary member 703. Deployment may take place in a gradual and easily controllable manner by enabling the practitioner to verify how deployment takes place.

In some embodiments, so long as the annular formation V2 of the valve V is still constrained within the formation 709 by the intermediate member 770, the practitioner still retains firm control (either directly or through the robotic system 100 discussed with respect to FIG. 2) of the partial (e.g., "basket-like") expanded valve V. The practitioner will thus be able to adjust the position of the valve V both axially and radially (e.g., by rotating the valve V around its longitudinal axis). This radial adjustment allows the practitioner to ensure that radially expanding anchoring formations of the valve V are properly aligned with the Valsalva sinuses to firmly and reliably retain in place the valve V once finally delivered.

With the valve V retained by the device 700 almost exclusively via the intermediate member 770 acting on the annular formation V2, the blocking member 702 can be removed from the shaft 706, thus permitting the inner sleeve 705, 707 (and, if not already effected previously, the outer sleeve 704, 708) to be retracted in such a way to disengage the annular portion V2 of the valve. This movement allows the annular formation V2 (and the valve V as a whole) to become disengaged from the device 700 and thus becoming completely deployed at the implantation site. This movement can be effected by sliding the inner sleeve (and the outer sleeve) towards the handle 701.

In some embodiments, delivery devices such as the delivery device 700 are described in U.S. patent application Ser. No. 12/465,262, filed May 13, 2009 and entitled 'DEVICE FOR THE IN SITU DELIVERY OF HEART VALVES', which application is hereby incorporated by reference herein in its entirety.

In some embodiments, a prosthetic aortic valve such as the valve 301 (described with respect to FIG. 3) or the valve 401 (described with respect to FIG. 4) may be implanted in a patient such as the patient 10 (FIG. 1) in a minimally invasive manner using a robotic system 100 (FIG. 2). In some embodiments, the valve may be disposed on a delivery device such as the delivery device 501 (FIG. 5) or the delivery device 700 (FIG. 7). In some cases, the delivery device may be manually operated or by the surgeon using the robotic system 100.

Figure 9:
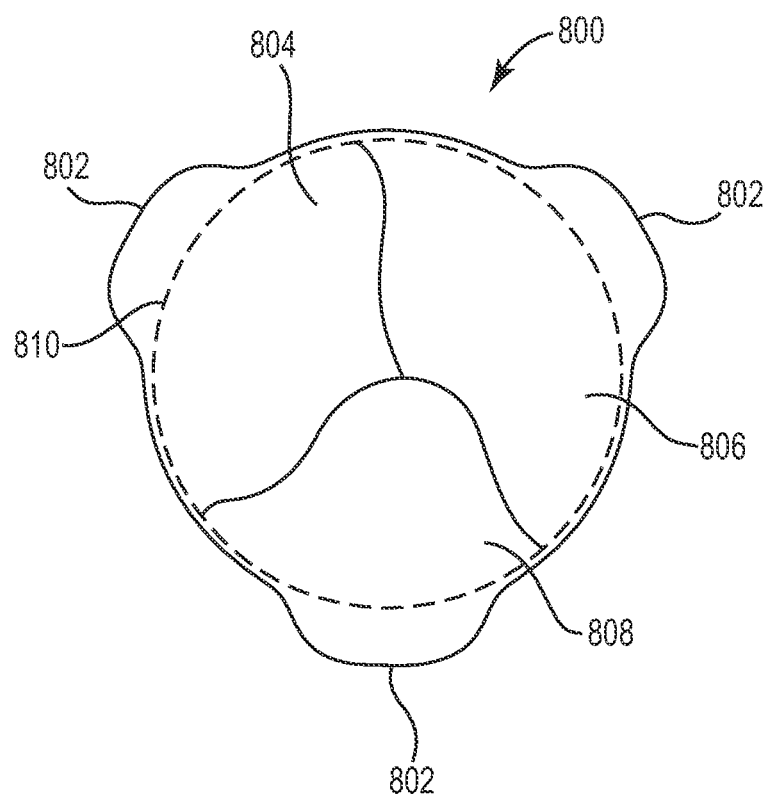
FIGS. 9 through 14 illustrate an implantation process.

FIG. 9 is a highly schematic illustration of a native aortic valve 800, viewed from a vantage point above the valve 800 (such as from within a transected aorta) such that the Valsalva Sinuses 802 are visible. Three native leaflets 804, 806 and 808 are illustrated in a closed position in which no or substantially no blood flow is permitted through the valve 800. A dashed line 810 diagrammatically illustrates the portions of the native tissue that are to be removed prior to implantation of the prosthetic aortic valve.

Figure 10:
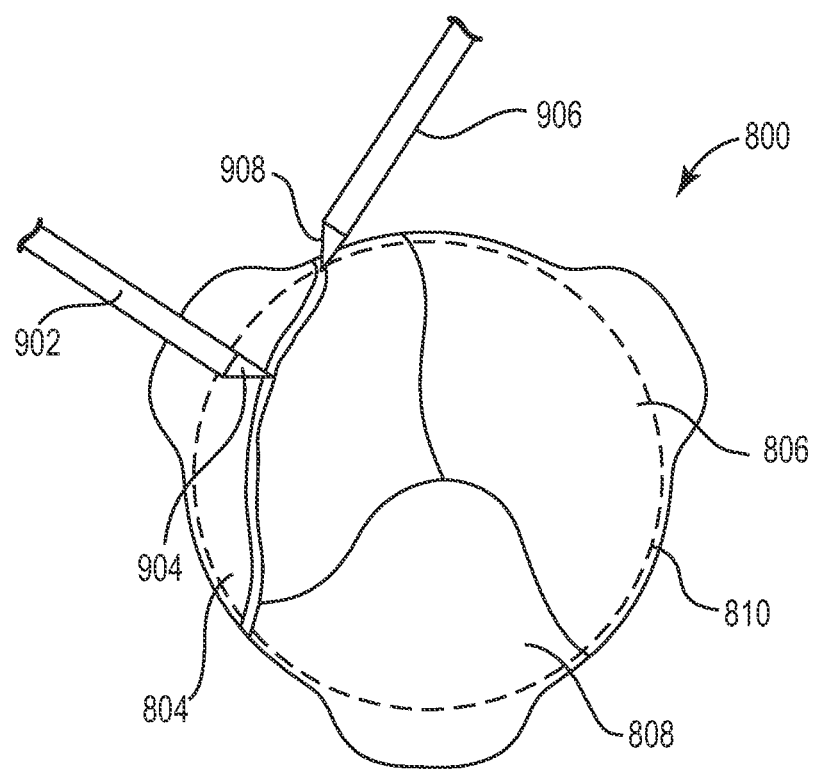

FIG. 10 is a highly schematic illustration of the native aortic valve 800 of FIG. 9, illustrating a step in tissue removal. In some embodiments, the native aortic valve 800 is reached in this manner by transecting a portion of the aorta. It can be seen that the native leaflet 804 has been pulled back and is grasped by a tool 902. The tool 902 has a distal end equipped with a pincers 904 that is configured to be able to grasp and hold tissue without, for example, tearing through the tissue. In some embodiments, the tool 902 may be considered as an embodiment of the tools 138, 139 discussed above with respect to FIG. 2.

A tool 906 has a distal end equipped with a cutting blade 908. It can be seen that the cutting blade 908 (which may also be considered as a manifestation of the previously discussed tools 138, 139) is cutting away the native leaflet 804 along the previously noted dashed line 810. While the removal of only one native leaflet 804 is illustrated, a similar process may be used to remove the other native leaflets 806 and 808, as well as to remove any other tissue as appropriate. While not illustrated in FIG. 10, in some embodiments a viewing instrument such as the camera 140 may be disposed within one of the access ports.

Figure 11:
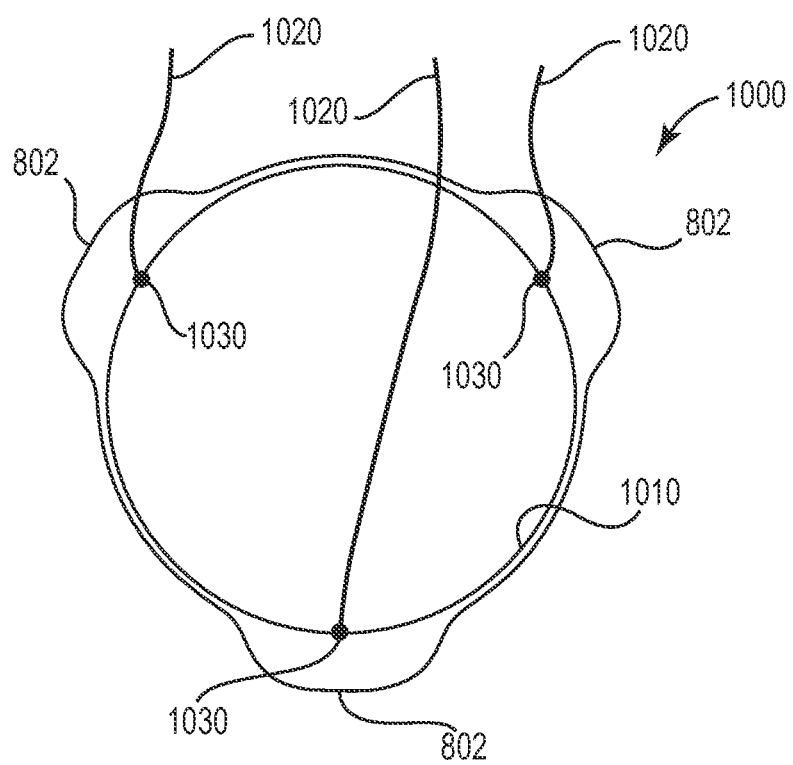

FIG. 11 illustrates the aortic annulus 1000 once the native leaflets 804, 806 and 808 have been removed, leaving an inner surface 1010 that corresponds to the placement of the dashed line discussed with respect to FIGS. 9 and 10. In some embodiments, valve replacement may include anchoring guide lines that can be used to guide the replacement valve into place. In some instances, the anchoring guide lines help to rotationally orient the replacement valve with respect to the Valsalva sinuses 802.

Figure 12:
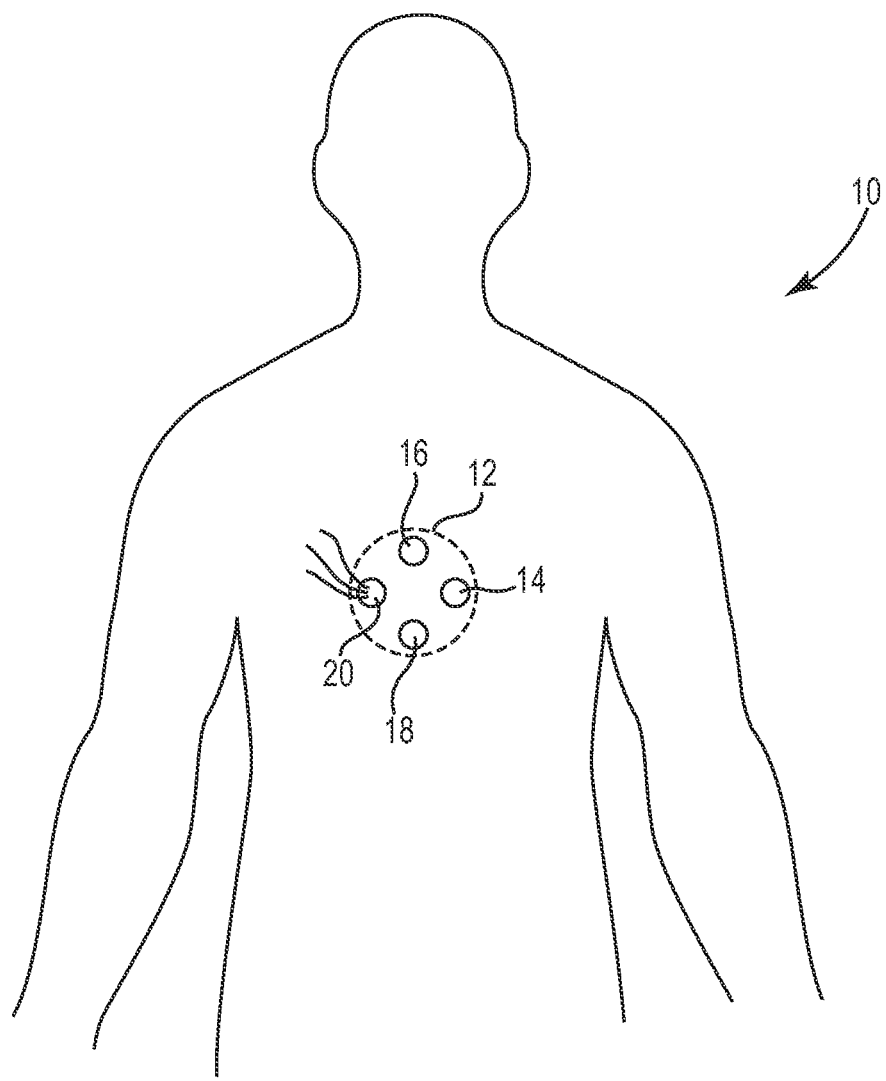

In the illustrated embodiments, sutures 1020 may extend from locations 1030 that are disposed near each of the Valsalva sinuses 802. The sutures 1020 may extend outwardly and may be secured to the valve prior to insertion of the valve using a delivery device. As seen in FIG. 12, the sutures 1020 may be seen as extending outwardly through the delivery port 20. The sutures 1020 may be secured to the valve. In some cases, the valve may include predetermined locations for attachment of the sutures 1020 in order to provide precise rotational positioning of the valve relative to the aortic annulus 1000. In some embodiments, the valve may include protrusions that are adapted to conform to the Valsalva sinuses 802 and the valve may include predetermined locations for attachment of the sutures 1020 to position the valve such that the protusions are located within the Valsalva sinuses 802.

Figure 13:
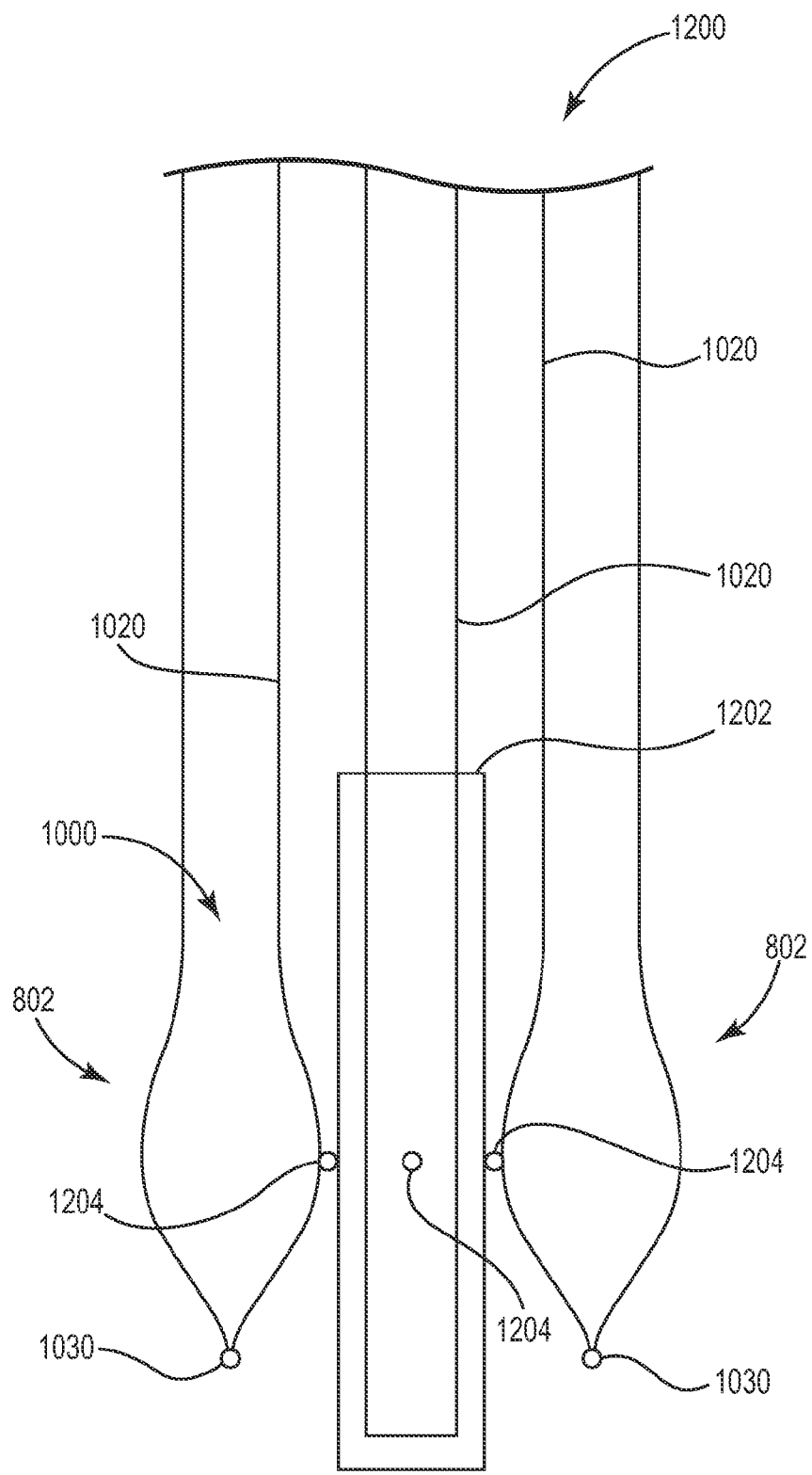

FIG. 13 is a highly schematic illustration of a delivery device 1200 (such as the delivery device 501 or the delivery device 700 discussed previously) that bears a prosthetic valve 1202 (such as the valve 301 or the valve 401) that has been inserted into position proximate the aortic annulus 1000. The threads 1020 are slidably secured to the prosthetic valve 1202 at locations 1204 so that the prosthetic valve 1202 may, under the control of the delivery device 1200, slide down the threads 1020. Once positioned, the prosthetic valve 1202 may be deployed as discussed above with respect to the delivery devices 501 and 700).

Figure 14:
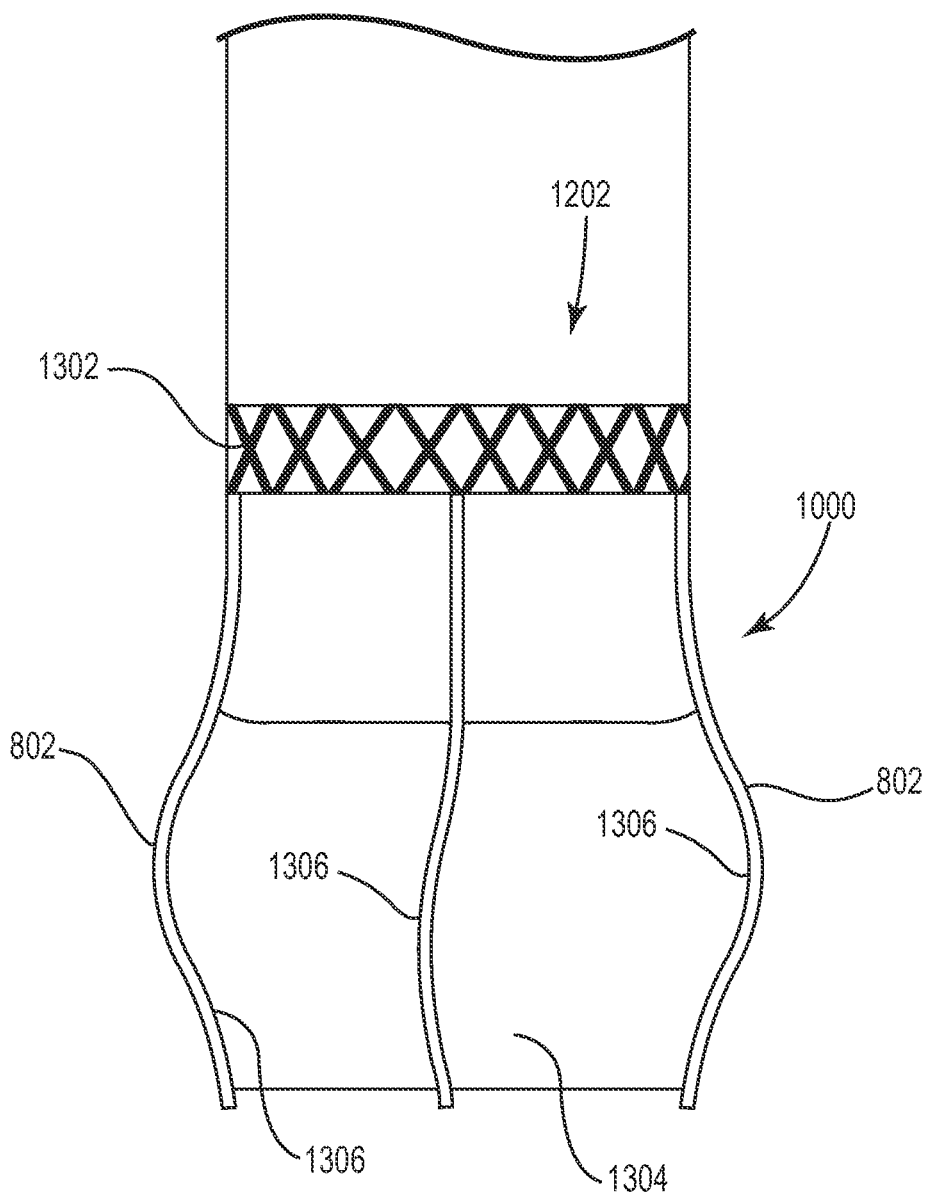

FIG. 14 is a highly schematic illustration of the prosthetic valve 1202 after deployment. The deployed prosthetic valve 1202 has a cage structure 1302 and a leaflet portion 1304. While not illustrated, the leaflet portion 1304 has, in some embodiments, a total of three leaflets. The cage structure 1302 includes several radially protruding portions 1306 that correspond to and interact with the Valsalva sinuses 802. In the illustrated embodiment, one of the Valsalva sinuses 802 is disposed along the left side of the aortic annulus 1000, one of the Valsalva sinuses 802 is disposed along the right side of the aortic annulus 1000 and the remaining Valsalva sinus 802 is located at a position extending outwardly from the page.

Figure 15:
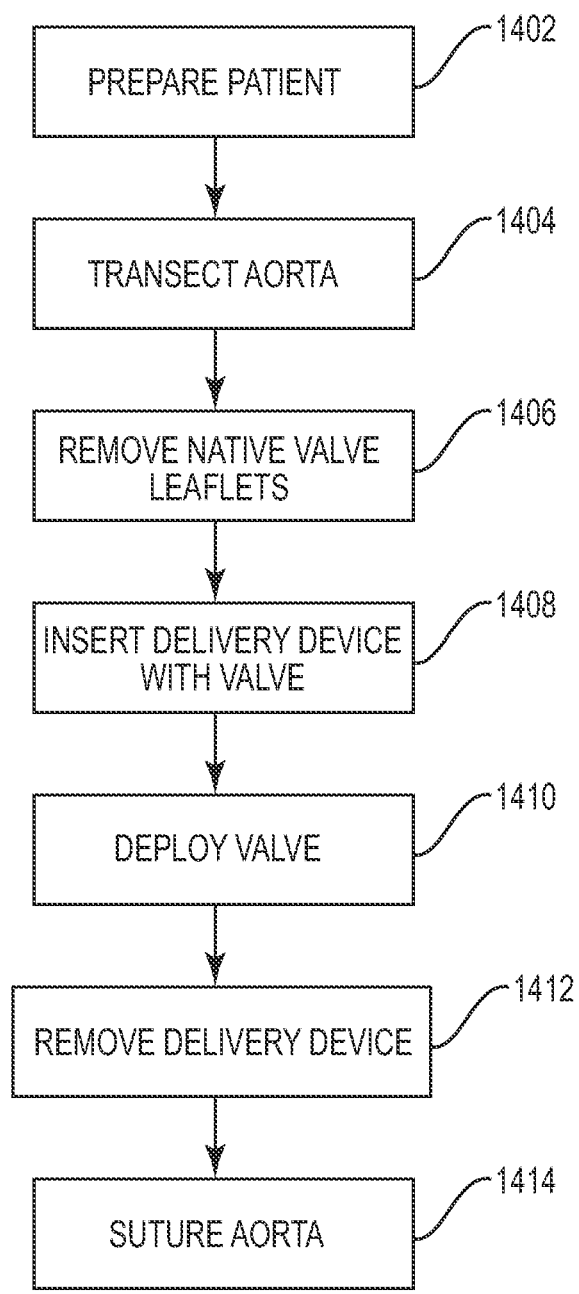
FIG. 15 is a flow diagram providing an illustrative method.

FIG. 15 is a flow diagram illustrating an implantation method that may be carried out using the prosthetic valves, delivery devices and robotic system described herein. At block 1402, a patient is prepped for a minimally invasive procedure that will utilize the robotic system 100. This step includes manually forming the access ports discussed above and inserting a camera or other viewing apparatus. The patient's aorta is transected through one or more of the access ports using the robotic system, as generally shown at block 1404. At block 1406, the robotic system is used to excise the native valve leaflets.

A prosthetic valve is loaded onto a delivery device, which is then inserted through one of the access ports (such as the delivery port 20), as shown at block 1408. In some embodiments, guide threads are secured to the aortic annulus and may be used to rotationally align the prosthetic valve. Once the prosthetic valve is properly positioned, the valve is deployed as shown at block 1410. At block 1412, the delivery device is withdrawn. The aorta is then sutured as generally shown at block 1414.

EXPERIMENTAL

The DaVinci S-HD system was used to open and suspend the pericardium anterior to the phrenic nerve in cadavers. A transthoracic cross clamp was placed across the mid-ascending aorta, following which a transverse aortotomy was made. The native aortic valve cusps were excised and annular calcium was removed with robotic instruments. Following placement of three guide-sutures a self-expanding bovine pericardial prosthesis in a nitinol frame was mounted on a flexible delivery system was inserted through a second intercostal space working port and lowered into the aortic annulus. Device positioning was confirmed using high definition video imaging of the inflow skirt. The aortotomy was closed with a double layer Prolene stitch using robotic instruments.

Successful implantation of all valves (N=5) was possible utilizing a 3 cm right second intercostal space working port, along with 2 additional 1 cm instrument ports (left arm & right arm). A standard transverse aortotomy was sufficient for examination/debridement of the native aortic valve cusps, sizing of the annulus and deployment of the nitinol-stented, bovine pericardial prosthesis. Delivery, seating and stability of the device were confirmed using high definition robotic imaging above and below the aortic valve annulus.

Complete excision of diseased native aortic valve cusps using robot assistance facilitates accurate and reproducible aortic valve replacement using a novel self-expanding sutureless version of a proven bovine pericardial prosthesis. This approach is comparable to the current surgical gold standard and is ready for clinical use as an alternative to percutaneous aortic valve implantation.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A minimally invasive method of implanting a self-expanding prosthetic aortic valve in a valve annulus, the method comprising the steps of:
    forming a surgical site within a patient's chest, the surgical site including a first access port, a second access port, a viewing port and a delivery port;
    inserting a camera into the viewing port, the camera adapted to provide images from within the surgical site in order to guide subsequent remotely operated steps;
    remotely grasping each of the native aortic valve leaflets with a remotely operated tissue grasping device inserted into one of the first and second access ports;
    remotely excising each of the grasped native aortic valve leaflets with a remotely operated cutting device inserted into another of the first and second access ports;
    remotely attaching sutures to tissue proximate the valve annulus, each suture at a location near a center of a corresponding one of a plurality of Valsalva sinuses;
    attaching the sutures to the self-expanding prosthetic aortic valve, the self-expanding prosthetic aortic valve including several protrusions, each protrusion adapted to conform to a corresponding Valsalva sinus;
    remotely delivering the self-expanding prosthetic valve to the valve annulus through the delivery port using a delivery device, the self-expanding prosthetic valve advancing along the sutures to rotationally locate the self-expanding prosthetic aortic valve relative to the valve annulus such that each protrusion is located within the corresponding Valsalva sinus;
    remotely implanting the self-expanding prosthetic aortic valve at the valve annulus; and
    remotely withdrawing the delivery device.

2. The method of claim 1, further comprising a step, after inserting the camera, of remotely transecting the patient's aorta to gain access to the native aortic valve.

3. The method of claim 2, wherein the step of remotely transecting the patient's aorta comprises cutting the aorta with the remotely operated cutting device.

4. The method of claim 1, further comprising a step, subsequent to withdrawing the delivery device, of remotely suturing the transected aorta.

5. The method of claim 1, wherein the step of implanting the self-expanding prosthetic aortic valve using the delivery device comprises using the delivery device to position and subsequently expand the self-expanding prosthetic aortic valve.

6. The method of claim 1, wherein at least some of the remotely performed steps are performed by a surgeon manipulating a control device that translates the surgeon's hand movements into operational commands for the remotely operated devices.

7. The method of claim 6, wherein the control device also scales the surgeon's hand movements.

8. A minimally invasive method of implanting a self-expanding prosthetic aortic valve in a valve annulus, the method comprising the steps of:
    forming a surgical site within a patient's chest, the surgical site including a first access port, a second access port, a viewing port and a delivery port;
    inserting a camera into the viewing port, the camera adapted to provide images from within the surgical site in order to guide subsequent remotely operated steps;
    remotely grasping each of the native aortic valve leaflets with a remotely operated tissue grasping device inserted into one of the first and second access ports;
    remotely excising each of the grasped native aortic valve leaflets with a remotely operated cutting device inserted into another of the first and second access ports;
    remotely attaching sutures to tissue proximate the valve annulus, each suture at a location near a center of a corresponding one of a plurality of Valsalva sinuses;
    attaching the sutures to the self-expanding prosthetic aortic valve, the self-expanding prosthetic aortic valve including several protrusions, each protrusion adapted to conform to a corresponding Valsalva sinus;
    advancing the self-expanding prosthetic valve to the valve annulus through the delivery port using a delivery device, the self-expanding prosthetic valve advancing along the sutures to rotationally locate the self-expanding prosthetic aortic valve relative to the valve annulus such that each protrusion is located within the corresponding Valsalva sinus; and
    remotely implanting the self-expanding prosthetic aortic valve at the valve annulus.

9. The method of claim 8, further comprising a step, after inserting the camera, of remotely transecting the patient's aorta to gain access to the native aortic valve.

10. The method of claim 9, wherein the step of remotely transecting the patient's aorta comprises cutting the aorta with the remotely operated cutting device.

11. The method of claim 8, further comprising a step of remotely suturing the transected aorta.

12. The method of claim 8, wherein at least some of the remotely performed steps are performed by a surgeon manipulating a control device that translates the surgeon's hand movements into operational commands for the remotely operated devices.

13. The method of claim 12, wherein the control device also scales the surgeon's hand movements.

* * * * *